(12) United States Patent
Muhlegger et al.

(10) Patent No.: US 6,329,346 B1
(45) Date of Patent: Dec. 11, 2001

(54) OLIGO-2'-DEOXYNUCLEOTIDES AND THEIR USE AS PHARMACEUTICAL AGENTS WITH ANTIVIRAL ACTIVITY

(75) Inventors: Klasu Muhlegger, Polling; Herbert Von Der Eltz, Weilheim; Frank Seela; Helmut Rosemeyer, both of Osnabruck, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 08/991,183

(22) Filed: Dec. 16, 1997

Related U.S. Application Data

(63) Continuation of application No. 08/150,109, filed on Apr. 20, 1994, now abandoned.

(30) Foreign Application Priority Data

May 25, 1991 (DE) .................................................. 41 17 186

(51) Int. Cl.[7] ............................. A01N 43/04; A61K 31/70
(52) U.S. Cl. .......................... 514/44; 536/23.1; 536/24.3; 536/24.5; 536/25.3; 536/25.32; 536/25.33
(58) Field of Search ............................... 514/44; 435/238; 536/23.1, 24.3, 24.5, 25.3, 25.33, 255, 25.32

(56) References Cited

U.S. PATENT DOCUMENTS

| | | | |
|---|---|---|---|
| 3,413,282 | 11/1968 | Yoshikawa | 536/25.33 |
| 5,212,295 | * 5/1993 | Cook | 536/26.7 |

OTHER PUBLICATIONS

Ginestar et al., New J. Chem. vol. 11, No. 11–12, 779–785 (1987) Abstract Only.*

Rosemeyer et al., Helvetica Chimica Acta, vol. 74 (1991) pp. 748–760, 1991.*

J. Med. Chem., Robins et al., "Nucleic Acid Related Compounds. 57. Synthesis, X-ray Crystal Structure, Lipophilic Partition Properties, and Antiretroviral Activities of Anomeric 3'-Azido-2,',3'-dideoxy-2,6-diaminopurine Ribosides", vol. 32, pp. 1763–1768 (1989).

Liebigs Ann. Chem., Vorbrüggen et al., "Einfache Neue Synthese von N[6]-substituierten Adenosinen und Adeninen Sowie lhrer 2-Amino-und 2-Hydroxyderivate**/3/", Heft. 4, pp. 745–761 (1976).

Helvetica Chemica Acta, Rosemeyer et al., "1-(2'-Deoxy-β-D-xylofuranosyl) thymine Building Blocks for Solid-Phase Synthesis and Properties of Oligo(2'-Deoxyxylonucleotides)", vol. 74, pp. 748–760 (1991).

Nucleic Acid Research, Froehler et al., "Synthesis of DNA via Deoxynucleoside H-phosphonate Intermediates", vol. 14, pp. 5398–5407 (Nov. 13, 1986).

J. Am. Chem. Soc., Tl et al., "Transient Protection: Efficient One–Flask Syntheses of Protected Deoxynucleosides", vol. 104, pp. 1316–1319 (1982).

Synthesis, Czernecki et al., "An Efficient Synthesis of 3'-Azido-3'-deoxythymidine (AZT)", pp. 239–240 (Mar. 1991).

J. Am. Chem. Soc., Hansske et al, "A Deoxygenative [1,2]-Hydride Shift Rearrangement Converting Cyclic cis-Diol Monotosylates to Inverted Secondary Alcohols", vol. 105, pp. 6736–6737 (1983).

Z.A. Shabarova "Chemical Development in the Design of Oligonucleotide Probes for Binding to DNA and RNA" (1988) Biochimie 70: 1323–1334.

Sokolova et al., "Dinucleoside Phosphates Containing Arabinoise or Deoxyxylose, Hydrolysis by Exonucleases and Stacking Properties", Nucleosides & Nucleotides, 9(4): 515–531 (1990).

Nakayama et al., Differential Inhibitory Effects of 5–Substituted 1–β–D–Xylofuranosyluracil 5–Triphosphates and Related Nucleotides on DNA–Dependent RNA Polymerases I and II from the Cherry Salmon (Oncorhynchus masou), J. Biochem. 98 (2)4:417–425 (1985).

Rosemeyer et al., 72.1–(2'–Deoxy–β–D–xylofuranosyl) thymine Building Blocks for Solid–Phase Synthesis and Properties of Oligo (2'–Deoxyxylonucleotides) Helvetica Chemica Acta 74:748–760 (1991).

Roseyemer et al., 192.9–(2'–Deoxy–β–D–xylofuranosyl) adenine Building Blocks for Solid–Phase Synthesis and Properties of Oligo (2'–Deoxyxylonucleotides), Helvetica Chemica Acta 74:2054–2067 (1991).

C.A. Stein et al., "Antisense Oligonucleotides as Therapeutic Agents—Is the Bullet Really Magical?", (1993) Science 261: 1004–1012.

P. Westermann et al., "Inhibition of Expression of SV40 Virus Large T–antigen by Antisense Oligodeoxyribonucleotides", (1989) Biomed Biochim Acta 48: 85–93.

R.A. Stull et al., "Antigene, Ribozyme and Aptamer Nucleic Acid Drugs: Progress and Prospects", (1995) Pharmaceutical Research 12: 465–483.

S. Wu–Pong "Oligonucleotides: Opportunities for Drug Therapy and Research", (1994) Pharmaceutical Technology 118:102–114.

(List continued on next page.)

*Primary Examiner*—James O. Wilson
(74) *Attorney, Agent, or Firm*—Arent Fox Kintner Plotkin & Kahn PLLC.

(57) ABSTRACT

Oligodeoxyribonucleotides in which at least two 2'-deoxy-β-D-erythro-pentofuranosyl groups are replaced by 2'-deoxy-β-D-threo-pentofuranosyl groups at both the 5' end and 3' end, and oligodeoxyribonucleotides in which at least 20% of the 2'-deoxy-β-D-erythro-pentofuranosyl groups in consecutive nucleotide building blocks are replaced by 2'-deoxy-β-D-threo-pentofuranosyl groups and which are composed of 6 to 100 nucleotide building blocks, are suitable for the inhibition of the expression of viral genes and oncogenes by the antisense principle and can be used for the production of pharmaceutical agents with antiviral activity.

27 Claims, 5 Drawing Sheets

OTHER PUBLICATIONS

R.W. Wagner "Gene Inhibition Using Antisense Oligodeoxynucleotides", (1994) Nature 372: 333–335.

H. Collins "It Stops the Virus—In A Test Tube", (Mar. 6, 1993) Philadelphia Inquirier p. A01.

J.S. Cohen "Oligonucleotide Therapeutics" (1992) Trends in Biotechnology 10:87–91.

B. Dropulic et al., "Gene Therapy for Human Immunodeficiency Virus Infection: Genetic Antiviral Strategies and Targets for Intervention", (1994) Human Gene Therapy 5:927–939.

P.A. Pizzo et al., "Antiretroviral Therapy for Infection Due to Human Immunodeficiency Virus in Children", (1994) Clinical Infectious Diseases 19:177–196.

E. R. Kern "Preclinical Evaluation of Antiviral Agents: In Vitro and Animal Model Testing" (1990) In: Antiviral Agents and Viral Diseases of Man, 3rd edition, G.J. Galasso et al., eds, pp. 94–95.

Sacramento Bee "Firm Curbs Aids—Drug Tests" (Nov. 29, 1991) p. B5.

Sacramento Bee "Anti–Aids Virus Drug Fails" (Feb. 26, 1995) P. A22.

E. Uhlmann et al., "Antisense Oligonucleotides: A New Therapeutic Principle" ('1990) Chemical Reviews 90: 543–584.

Hansske et al., "A Deoxygenative [1,2]–Hydribe Shift Rearrangement Converting Cyclic cis–Diol Monotosylates to Inverted Secondary Alcohols", J. Am. Chem. Soc. 105:6736–6737 (1983).

* cited by examiner

OLIGO-2'-DEOXYNUCLEOTIDES AND THEIR USE AS PHARMACEUTICAL AGENTS WITH ANTIVIRAL ACTIVITY

The present application is a continuation application of application Ser. No. 08/150,109, filing date Apr. 20, 1994 which has been abandoned.

Oligonucleotides whose sequences are complementary to the RNA or DNA of a viral sequence or to an oncogene are of potential interest for the therapy of viral infections since they can inhibit the expression of viral genes. The underlying method, denoted antisense principle, is described for example by Zamecnik, P. C. and Stephenson, M. L. (1978) in Proc. Natl. Acad. Sci. USA 75, 280.

However, it has turned out that when such antisense oligonucleotides are introduced into cells, preferentially intrinsic cell enzymes rapidly degrade these oligonucleotides by cleavage of phosphodiester bridges, and they thus become ineffective.

Therefore many attempts have been made to synthesize antisense oligonucleotides which are resistant to enzymatic degradation (Uhlmann, E. and Peyman, A. (1990) in "Antisense oligonucleotides: A new therap. Principle", Chem. Rev. 90, 543–584). Up to now such modifications have been primarily carried out at the internucleotide bridges i.e. on the phosphorus atom. Thus for example oligonucleoside-phosphorothioates and -oligonucleoside-phosphorodithioates, as well as non-ionic oligonucleoside-methylphosphonates, oligonucleoside-methylphosphorothioates, oligonucleoside-alkylphosphotriesters and oligonucleoside-alkylphosphoramidates have been described which are resistant to enzymatic degradation. A disadvantage of these compounds is for example their chirality with regard to the phosphorus atom. This means that in each case there are two pairs of diastereoisomers. This non-uniformity, however, limits their pharmacological effectiveness or requires a complicated separation of the isomers before use as therapeutic agents.

A further known class of compounds which has been proposed for antisense therapy are oligonucleotides which contain intercalating or reactive ligands. Thus for example acridine-modified oligomers or oligonucleotides which can be cross-linked (psoralenazidoproflavin-substituted) have been described (Hélène, C. and Thuong, N. T. in "Antisense RNA and DNA", Curr. Commun. Mol. Biol.; Cold Spring Harbor Laboratory, Cold Spring Harbor N.Y., 1987). The production of such oligonucleotides is, however, very complicated.

In addition it is known that those oligodeoxynucleotides which have a configuratively changed glyconic part (alpha DNA) can be used as antisense oligonucleotides. Such an alpha DNA which is comprised exclusively of purine-2'-deoxynucleosides and pyrimidine-2'-deoxynucleosides in the alpha-D configuration is not or only very slowly degraded by intrinsic cell enzymes and would therefore be suitable for antisense therapy. However, a disadvantage of these compounds is the very complicated and tedious synthesis (Cohen, J. S. in Topics in Molecular and Structural Biology, "Oligonucleotides: Antisense Inhibitors of Gene Expression", MacMillan Press, Lt. 1989). In addition dinucleotide monophosphates are known which are resistant to nucleases due to a building block in the threo configuration (Sokolova et al.; Nucleosides and Nucleotides 9/4 (1990), 515–531). However, corresponding oligonucleotides are neither disclosed nor would it be possible to produce these without difficulty. In addition the dinucleotides are not suitable for hybridization and formation of duplexes.

The object of the present invention was therefore to provide oligonucleotides which are not enzymatically degraded in eukaryotic cells, which can be easily produced and are suitable as pharmaceutical antiviral agents based on the antisense principle.

The invention therefore concerns oligodeoxyribonucleotides in which at least two 2'-deoxy-β-D-erythro-pentofuranosyl groups are replaced by 2'-deoxy-β-D-threo-pentofuranosyl groups at both the 5' and 3' end and which are composed of 6 to 100 nucleotide building blocks.

The invention in addition concerns oligodeoxyribonucleotides in which at least 20% of the 2'-deoxy-β-D-erythro-pentofuranosyl groups are replaced by 2'-deoxy-β-D-threo-pentofuranosyl groups in consecutive nucleotide building blocks and which are composed of 6–100 nucleotide building blocks.

Surprisingly such oligonucleotides (also denoted oligonucleotides in the following) are resistant or substantially resistant to nucleolytic degradation by cellular enzymes such as for example phosphodiesterases, exonucleases and endonucleases. In addition they form stable double-stranded hybrid structures with natural 2'-deoxyribonucleotides under the natural conditions in eukaryotic cells although they presumably at least in part have left-helical DNA structures as demonstrated by their CD spectra. The oligonucleotides according to the present invention are suitable for inhibiting the expression of viral genes and oncogenes in eukaryotic cells and can therefore be used therapeutically as antisense oligonucleotides.

30% and particularly preferably all of the 2'-deoxy-β-D-erythro-pentofuranosyl groups are replaced by 2'-deoxy-β-D-threo-pentofuranosyl groups.

If all the 2'-deoxy-β-D-erythro-pentofuranosyl groups are replaced by 2'-deoxy-β-D-threo-pentofuranosyl groups in an oligonucleotide, it is expedient that this oligonucleotide be designated an oligodeoxyxylonucleotide.

The structure of such an oligonucleotide according to the present invention is shown schematically in FIG. 1 (section from an oligodeoxyxylonucleotide).

In the following the nucleotides which contain 2'-deoxy-β-D-erythro-pentofuranosyl groups are designated 2'-deoxyribonucleotides and the nucleotides which contain 2'-deoxy-β-D-threo-pentofuranosyl groups are designated 2'-deoxyxylonucleotides or building blocks.

In addition 2'-deoxyribonucleotide building blocks are referred to as dB (e.g. dA, dT, dC, dG) and 2'-deoxyxylonucleotide building blocks are referred to as dxB (e.g. dxA, dxT, dxC, dxG).

It is preferred that the dxBs and dBs occur consecutively in blocks in the oligonucleotides according to the present invention.

Accordingly preferred oligonucleotides according to the present invention are:

d {xBcB(B)$_n$xBxB} d {(B)$_m$(xB)$_n$(B)$_o$} d {(xB)$_m$(B)$_n$(xB)$_o$} in which n, m and o is at least 4, provided that the total length of the oligonucleotides according to the present invention does not exceed 100 nucleotide building blocks.

In an equally preferred embodiment, one or several nucleotide building blocks dB can be replaced by dxB at specific positions on the oligonucleotide (e.g. recognition sequences of endonucleases) in order to prevent cleavage by endonucleases.

All natural or modified nucleobases are suitable as bases. Particularly preferred modified bases are 5-methylcytosine or deazapurine such as 1-deazaadenine, 3-deazaadenine, 7-deazaadenine, 1-deazaguanine, 3-deazaguanine, 7-deazaguanine, 1-deazahypoxanthine, 3-deazahypoxanthine, 7-deazahypoxanthine and those bases which are substituted at the C-5 of pyrimidines, at the C-7 in the case of 7-deazapurines or at the C-8 of purines.

In addition the oligonucleotides according to the present invention can contain modifications at the internucleotide bridges in which case the modifications are preferably present at all internucleotide bridges of the oligonucleotide according to the present invention. In this connection phosphorothioates, methylphosphonates and phosphoroamidates are preferred.

The 3' and/or 5' ends the oligonucleotides according to the present invention can contain all suitable terminal groups known to a person skilled in the art. Hydrogen, mono-, di- or triphosphate, a reporter group or an intercalator group is preferred for the 3' end and for the 5' end. The other nucleotide building blocks can also be modified by reporter groups or intercalator groups.

A reporter group within the meaning of the invention is understood as a hapten such as e.g. biotin or digoxigenin or a fluorescent dye residue. Suitable intercalator groups are described by Hélène, C., loc. cit. and are preferably phenanthroline, acridine, actinomycin or its chromophore or heavy metal complexing agents such as EDTA. Those groups which lead to cross-linking of nucleic acids such as e.g. psoralen are also advantageous.

Oligonucleotides according to the present invention are preferably composed of 15 to 30 nucleotide building blocks. The sequence of bases in the oligonucleotides according to the present invention depends on the sequence of the virus or oncogene towards which the oligonucleotide is intended to be directed. Thus for example oligonucleotides according to the present invention are particularly suitable for the therapy of HIV I infections in which all bases represent A or T and all 2'-deoxy-β-D-erythro-pentofuranosyl groups are replaced by 2'-deoxy-β-D-threo-pentofuranosyl groups since the viral sequence of HIV I contains several clusters with poly A or poly T sequences. Further particularly preferred oligonucleotides are those which are complimentary to certain genome regions which are important for the replication of viral genes. In the case of the HIV genome these are for example the regulatory region of the rev gene (Matsukura, M. et al. (1989) Proc. Natl. Acad. Sci. USA, 86, 4244).

The oligonucleotides according to the present invention are produced in a well-known manner for example by the phosphate triester, phosphite triester or H-phosphonate method in a homogeneous phase or on a support. The two latter methods are preferably used in which the synthesis is usually carried out using automated synthesizers.

The invention therefore in addition concerns a process for the production of oligodeoxyribonucleotides in which at least two 2'-deoxy-β-D-erythro-pentofuranosyl groups are replaced by 2'-deoxy-β-D-threo-pentofuranosyl groups at both the 5' and 3' end and which are composed of 6 to 100 nucleotide building blocks by means of the process of oligonucleotide synthesis in which a start nucleoside is bound to a solid support and subsequently the desired oligonucleotide is synthesized by stepwise coupling using appropriate activated monomeric nucleotide building blocks, if desired trivalent phosphorus is oxidized to pentavalent phosphorus during or after the synthesis, the oligonucleotide is cleaved from the support using a first base, heterocyclic protecting groups are cleaved with a second base, the 5' protecting group is cleaved with an acid and the oligonucleotide is purified if desired.

The invention in addition concerns a process for the production of oligodeoxyribonucleotides in which at least 20% of the 2'-deoxy-β-D-erythro-pentofuranosyl groups are replaced by 2'-deoxy-β-D-threo-pentofuranosyl groups in consecutive nucleotide building blocks and which are composed of 6 to 100 nucleotide building blocks by a process of oligonucleotide synthesis in which a start nucleoside is bound to a solid support and subsequently the desired oligonucleotide is synthesized by stepwise coupling using appropriate activated monomeric nucleotide building blocks, if desired trivalent phosphorus is oxidized to pentavalent phosphorus either during or after the synthesis, the oligonucleotide is cleaved from the support using a base, heterocyclic protecting groups are cleaved with a second base, the 5' protecting group is cleaved with an acid and the oligonucleotide is purified if desired.

Oligonucleotides are preferably produced which are composed of 15 to 30 nucleotide building blocks.

It is expedient to oxidize trivalent phosphorus to pentavalent phosphorus after each coupling of a nucleotide building block when using phosphoramidites as nucleotide building blocks or after synthesis of the total oligonucleotide when using phosphonates as nucleotide building blocks. Iodine (e.g. iodine/$H_2O$/lutidine) or, in the case of the production of 2'-deoxyxylonucleoside-3'-phosphorothioates and -3'-phosphorodithioates, sulphurization reagents (e.g. sulphur in pyridine/carbon disulphide) are preferably used for the oxidation.

Ammonia at 60° C. is preferably used for the alkaline cleavage; in order to remove the 5' protecting group, 80% aqueous acetic acid or tetrabutylammonium fluoride, in the case of a silyl protecting group is preferably used at room temperature.

After cleavage by base or acid it is expedient to neutralize and purify. Reverse phase HPLC or anion exchange HPLC is preferably used for the purification in which case it is subsequently desalted.

The procedure for such oligonucleotide syntheses is generally known to a person skilled in the art and is described for example by Gait, M. J. in "Oligonucleotide synthesis, a practical approach", IRL Press, LTD. 1984, Narang, S. A., "Synthesis and application of DNA and RNA", Academic Press 1987.

The supporting material is composed of inorganic (Controlled Pore Glas, Fractosil®) or organic polymeric material (e.g. polystyrene) known to a person skilled in the art.

In order to produce the oligonucleotides according to the present invention, a monomeric 2'-deoxyxylonucleoside or 2'-deoxyribonucleoside, which serves as the start nucleoside for the oligonucleotide synthesis, is preferably coupled to the supporting material by means of a coupling reagent (cf. e.g. Gait, M. J. loc.cit.).

A further process for the production of the oligonucleotides according to the present invention is the phosphate triester method (cf. Gait, M. J. loc.cit.).

The invention in addition concerns 2'-deoxyxylonucleoside-3'-phosphoroamidites, -3'-H-phosphonates and -P-methyl-phosphoroamidites protected by bases and sugars. These compounds are suitable as nucleotide building blocks for the production of the oligonucleotides according to the present invention.

The nucleotide building blocks according to the present invention particularly preferably contain the bases adenine, guanine, cytosine, thymidine, uracil, 5-methyl-cytidine or deazapurines such as e.g. 1-deazaadenine, 3-deazaadenine, 7-deazaadenine, 1-deazaguanine, 3-deazaguanine and 7-deazaguanine. Further preferred bases are those which are substituted at the C-5 of pyrimidines, at the C-7 of 7-deazapurines or at the C-8 of purines.

The nucleotide building blocks according to the present invention preferably contain protecting groups on the heterocyclic bases, 5'-OH or 3'-OH protecting groups.

Amino protecting groups such as e.g. benzyl, formamidine, isobutyryl or phenoxyacetyl group are preferably used as protecting groups on the heterocyclic bases.

A triphenylmethyl, monomethoxytrityl, dimethoxytrityl, t-butyl-dimethylsilyl, t-butyldiphenylsilyl, t-butyl-methoxyphenylsilyl or pixyl group is preferably used as the 5'-OH protecting group of the sugar part.

3'-O-(2-cyanoethyl)-N,N-diisopropyl-aminophosphanes and 3'-O-methyl-N,N-diisopropylamino-phosphanes are preferred as phosphoramidites. The H-phosphonates are preferably used as salts.

In a particularly preferred embodiment the nucleotide building blocks according to the present invention are labelled with $^{32}P$ or $^{35}S$.

The nucleotide building blocks according to the present invention which are capable of coupling are produced from the corresponding 2'-deoxyxylonucleosides (produced for example analogously to Fox and Miller J. Org. Chem. 28 (1963) 936, Hansske and Robins J. Am. Chem. Soc. 105 (1983) 6736–6737 or F. Seela and H. P. Muth, Helvetica Chimica Acta 74 (1991) 1081–1090).

The production of monomeric nucleotide building blocks is carried out according to methods familiar to a person skilled in the art, for example as described in Gait, M. J. loc.cit.

The oligonucleotides according to the present invention can be elongated at the 3' and/or 5' end by ligation with further oligonucleotides according to the present invention or known oligonucleotides. Such ligation reactions using DNA or RNA ligase are familiar to a person skilled in the art and described for example in Maniatis et al., Molecular Cloning, A Laboratory Manual, Cold Spring Harbor Laboratory, New York (1982). The oligonucleotides according to the present invention can also be produced enzymatically using a DNA polymerase and/or RNA polymerase. In this case nucleotides having the general formula

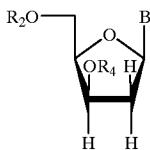

are used in which B represents A, T, C, G or a base from the group comprising 1-deazaadenine, 3-deazaadenine, 7-deazaadenine, 1-deazaguanine, 3-deazaguanine, 7-deazaguanine, 1-deazahypoxanthine, 3-deazahypoxanthine, 7-deazahypoxanthine, 7-deazapurines substituted at C-7, purines substitued at C-8, pyrimidines substituted at C-5, $R_1$ represents a hydrogen atom or a reporter group or an intercalator group and $R_2$ represents a mono-, di- or triphosphate.

The invention therefore in addition concerns nucleotides having the general formula

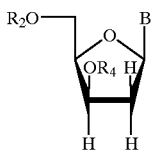

in which B represents A, T, C, G or a base from the group comprising 1-deazaadenine, 3-deazaadenine, 7-deazaadenine, 1-deazaguanine, 3-deazaguanine, 7-deazaguanine, 1-deazahypoxanthine, 3-deazahypoxanthine, 7-deazahypoxanthine, 7-deazapurines substituted at C-7, purines substituted at C-8, pyrimidines substituted at C-5, $R_1$ represents a hydrogen atom or a reporter group or an intercalator group and $R_2$ represents a mono-, di or triphosphate.

The invention in addition concerns the use of oligodeoxyribonucleotides in which at least two 2'-deoxy-β-D-erythro-pentofuranosyl groups are replaced by 2'-deoxy-β-D-threo-pentofuranosyl groups at both the 5' and 3' end and which are composed of 6 to 100 nucleotide building blocks for the production of a pharmaceutical agent with antiviral activity.

In addition the invention concerns oligodeoxyribonucleotides in which at least 20% of the 2'-deoxy-β-D-erythro-pentofuranosyl groups are replaced by 2'-deoxy-β-D-threo-pentofuranosyl groups in consecutive nucleotide building blocks and which are composed of 6–100 nucleotide building blocks for the production of a pharmaceutical agent with antiviral activity.

The oligonucleotides according to the present invention and their salts can be used as medicines, e.g. in the form of pharmaceutical preparations which can be administered orally e.g. in the form of tablets, coated tablets, hard or soft gelatin capsules, solutions, emulsions or suspensions. They can also be administered rectally e.g. in the form of suppositories or parenterally e.g. in the form of solutions for injections. In order to produce pharmaceutical preparations, these compounds can be processed in therapeutically inert organic and inorganic vehicles. Examples of such vehicles for tablets, coated tablets and hard gelatin capsules are lactose, maize starch or derivatives thereof, tallow, stearic acid or salts thereof. Suitable vehicles for the production of solutions are water, polyols, sucrose, inverted sugar and glucose. Suitable vehicles for injection solutions are water, alcohols, polyols, glycerol and vegetable oils. Suitable vehicles for suppositories are vegetable oils and hardened oils, waxes, fats and semi-liquid polyols.

The pharmaceutical preparations can also contain preservatives, solvents, stabilizing agents, wetting agents, emulsifiers, sweetners, dyes, flavouring materials, salts to alter the osmotic pressure, buffers, coating agents or antioxidants as well as if desired, other therapeutically active substances.

The invention is elucidated further by the following examples and figures:

BRIEF DESCRIPTION OF THE DRAWINGS

FIG. 2 shows the hydrolysis of the oligonucleotide d(GTAGAAxTxTCTAC) by calf spleen phosphodiesterase (H=hypochromicity of the final product obtained, the inserted figure shows the elution profile of the HPLC of the final product, a=(Et$_3$NH)OAc pH 7/acetonitrile (95:5), b=0–20% acetonitrile in mobile solvent a.

EXAMPLE 1

1-(2'-deoxy-β-D-threo-pentofuranosyl)thymine

Figure 1:
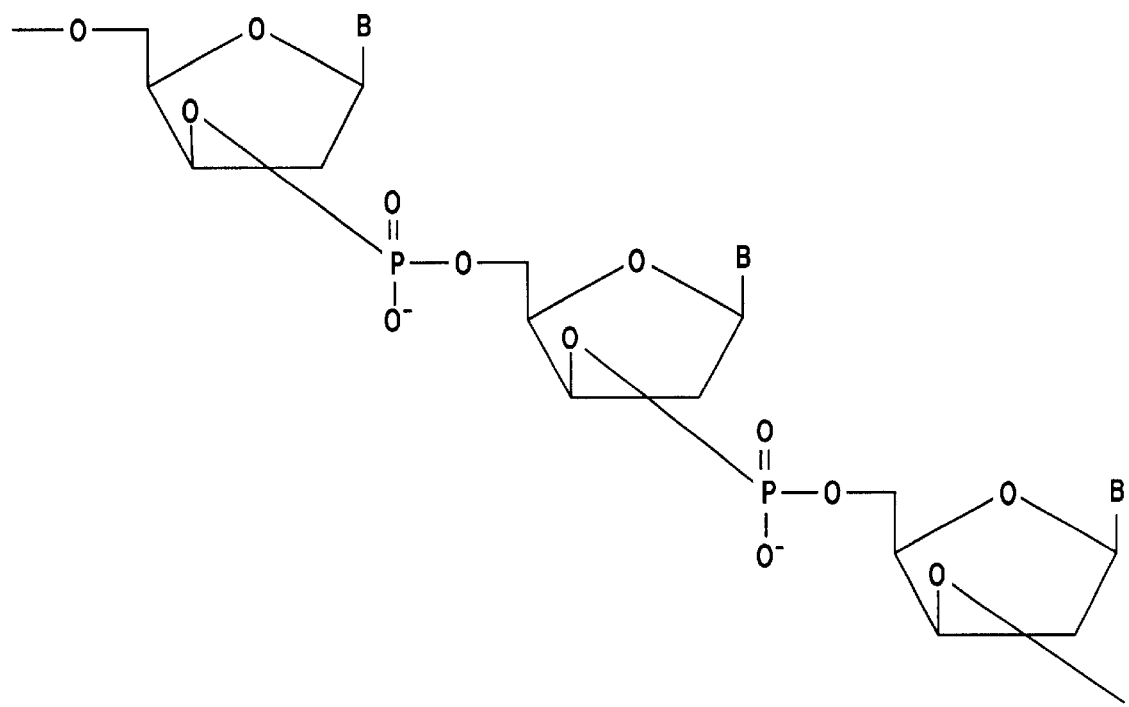
FIG. 1 shows a section from an oligodeoxyxylonucleotide.

The synthesis was carried out according to Fox and Miller [J. Org. Chem. (1963), 28, 936].

The product (dissolved in ($D_6$)DMSO) is characterized by the following signals in the $^1$H-NMR spectrum (results for δ in ppm): 11.25 (s, br. NH); 7.80 (s, H—C(6)); 6.06 (dd, J(H—C(1'), $H_β$—C(2')=2.7 Hz, J(H—C(1'),$H_α$—C(2')=5.5 hz, H—C(1')); 5.25 (3'-OH); 4.69 (5'-OH); 4.23 (m, H—C (3')); 3.76 (m, H—C(4')); 3.70 (m, $H_2$—C(5')); ca.2.5 ($H_α$—C(2')); 1.84 (d, J($H_β$—C(2'), $H_α$—C(2')=−16.0 Hz, $H_β$—C (2')); 1.66 (s, $CH_3$).

EXAMPLE 2

1-[2'-deoxy-5'-(4,4-dimethoxytriphenylmethyl)-β-D-threo-pentofuranosyl]-thymine 500 mg 1-(2'-deoxy-β-D-threo-pentofuranosyl)thymine (2.06 mmol) were dried by co-evaporating several times with anhydrous pyridine (5 ml in each case). The oily residue was dissolved in 15 ml anhydrous pyridine and admixed successively with 1.0 g 4,4'-dimethoxytriphenylmethyl chloride (3 mmol) and 0.5 ml diisopropylethylamine (3 mmol). It is stirred for 3 hours at 40° C. under nitrogen, afterwards the solution is poured into 50 ml 5% aqueous $NaCHO_3$ and extracted twice with 100 ml dichloromethane each time. The combined organic phases are dried over sodium sulfate and the solvent is removed by evaporation. After co-evaporating several times with toluene, the residue is purified on silica gel 60H by means of flash chromatography (column: 6×15 cm, $CH_2Cl_2$—MeOH, 98:2). The fractions which contained the main product are concentrated to a colourless, foamy residue (780 mg, 69% of theoretical yield).

TLC (silica gel, $CH_2Cl_2$—MeOH, 95:5) $R_f$ 0.6.

The product (dissolved in ($D_6$)DMSO) is characterized by the following signals in the $^1$H-NMR spectrum (results for δ in ppm): 11.30 (s, NH); 7.62 (s, H—C(6)); 7.45–6.86 (m, 13H, aromat. H); 6.12 (dd, J=6.2, 2.7 Hz, H—C(1')); 5.22 (d, J=3.4 Hz, 3'-OH); 4.20 (m, H—C(3')); 4.10 (m, H—C(4')); 3.73 (s, 6H, 2×$OCH_3$); 3.40 and 3.19 (2m, $H_2$—C(5')); ca. 2.51 (m, $H_α$—C(2')); 1.87 (d, J=−15.4 Hz, $H_β$-2'); 1.66 (s, $CH_3$).

Elemental analysis for $C_{31}H_{32}N_2O_7$ (544.6): calculated: C, 68.37; H, 5.92; N, 5.14. found: C, 68.44; H, 6.00; N, 5.15.

EXAMPLE 3

1-[(2'-deoxy-β-D-threo-pentofuranosyl-5'-O-(4,4'-dimethoxytriphenylmethyl)]-thymine-(3'-H-phosphonate), triethylammonium salt 1.06 g 1,2,4-triazole (15.3 mmol) was added to a solution of 0.4 ml phosphorus oxytrichloride (4.6 mmol) and 5.1 ml N-methylmorpholine (46 mmol) in 36 ml dichloromethane. After stirring for 30 minutes, the solution is cooled to 0° C. and a solution of 500 mg 1-[2'-deoxy-5'-(4,4'-dimethoxytriphenylmethyl)-β-D-threo-pentofuranosyl]-thymine in 12 ml dichloromethane is slowly added to this. After stirring for a further 10 minutes at room temperature, the reaction mixture is poured into 50 ml 1 M aqueous triethylammonium bicarbonate solution, pH 8.0, shaken and the phases are separated. The aqueous phase is extracted with 30 ml $CH_2Cl_2$ and the combined organic extracts are dried over $Na_2SO_4$ and evaporated to a colourless foam. Flash chromatography on silica gel 60H (column: 6×15 cm, firstly with $CH_2Cl_2$—$Et_3N$, 92:8, then with $CH_2Cl_2$—MeOH—$Et_3N$, 88:10:2) yielded a main fraction which was pooled and concentrated by evaporation. The residue was dissolved in 15 ml $CH_2Cl_2$ and extracted twice with 1 M aqueous triethylammonium bicarbonate solution, pH 8.0, the organic phases were dried over sodium sulfate and concentrated by evaporation. 480 mg (74% of theoretical yield) of the desired product is obtained in the form of a colourless foam.

TLC (silica gel, $CH_2Cl_2$—MeOH—$Et_3N$, 88:10:2): $R_f$ 0.3.

The product (dissolved in ($D_6$)DMSO) is characterized by the following signals in the $^1$H-NMR spectrum (results for δ in ppm): 11.30 (s, NH); 7.66 (s, H—C(6)); 7.63–6.86 (m, 13H, aromat. H), 6.13 (dd, J=6.8, 2.8 Hz, H—C(1')); 5.76 and 5.28 (d, J=119 Hz, PH); 4.62 (m, H—C(3')); 4.12 (m, H—C(4')); 3.73 (s, 6H, 2×$OCH_3$); 3.34 and 3.16 (m, $H_2$—C (5')); 2.73 (q, $CH_3CH_2NH$); ca. 2.5 (m, $H_α$—C(2')); 2.14 (d, J=−15.2 Hz, $H_β$—C(2')); 1.66 (s, $CH_3$); 1.03 (t, $CH_3CH_2NH$).

$^{31}$P-NMR (($D_6$)DMSO): 0.88 ppm ($^1$J(P—H)=587 Hz; $^3$J(P—H-4')=8.8 Hz).

Elemental analysis for $C_{37}H_{48}N_3O_9P$ (709.8): calculated: C, 62.61; H, 6.82; N, 5.92. found: C, 62.81; H, 7.00; N, 5.99.

EXAMPLE 4

1-[2'-deoxy-5'-O-(4,4'-dimethoxytriphenylmethyl)-β-D-threo-pentofuranosyl]-thymine-3'-[(2-cyanoethyl)-N,N-diisopropyl-phosphoramidite]

45 μl chloro-β-cyanoethoxy-(N,N-diisopropylamino)-phosphane (0.2 mmol) is added dropwise over a period of 2 minutes under nitrogen at room temperature to a solution of 100 mg 1-[2'-deoxy-5'-(4,4'-dimethoxytriphenylmethyl)-β-D-threo-pentofuranosyl]-thymine (0.18 mmol) and 0.1 ml N-ethyldiisopropylamine (0.57 mmol) in dry tetrahydrofuran. It is stirred for 30 minutes and afterwards the reaction is stopped by addition of 4 ml 5% aqueous $NaHCO_3$. The reaction mixture is extracted twice with 5 ml $CH_2Cl_2$ each time. The combined organic phases are dried over sodium sulfate and concentrated by evaporation. Flash chromatography (silica gel 60H, column: 3×6 cm, ethyl acetate-$CH_2Cl_2$—$Et_3N$, 45:45:10) yields two partially overlapping main fractions of the diastereomers (95 mg, 72% of theoretical yield).

TLC (silica gel, $CH_2Cl_2$—EtOAc—$Et_3N$, 45:45:10) $R_f$ 0.7 and 0.6.

$^{31}$P-NMR ($CDCl_3$): 148.5 ppm (more mobile compound in TLC); 151.8 ppm (less mobile compound in TLC).

EXAMPLE 5

9-(2'-deoxy-β-D-xylofuranosyl)adenine(2'-deoxyxyloadenosine)

The compound was prepared according to the instructions of Hansske and Robins [J. Am. Chem. Soc. (1983), 105, 6736–6737].

The product (dissolved in $(D_6)$DMSO) is characterized by the following signals in the $^1$H-NMR spectrum (results for δ in ppm): 8.35 (s, H—C(8)); 8.15 (H—C(2)); 7.34 (s, br., NH$_2$) 6.25 (dd, J(H—C(1'),H$_α$—C(2'))=2.2 Hz; J(H—C(1'), H$_β$—C(2'))=8.7 Hz; H—C(1')); 5.97 (s, br. 3'-OH); 4.69 (s, br., 5'-OH); 4.33 (m, H—C(3')); 3.89 (m, H—C(4')); 3.67 (m, H$_2$—C(5')); 2.78 (m, H$_α$—C(2')); 2.25 (dd, J(H$_α$—C(2'), H$_β$—C(2'))=−14.5 Hz; H$_β$—C(2')).

EXAMPLE 5a

2'-deoxy-xylo-inosine

2'-deoxy-xylo-adenosine (78 mg, 0.31 mmol) is suspended in 3 ml water and admixed with adenosine deaminase (calf spleen, 50 μg). It is stirred for 2 h at room temperature and evaporated to dryness; yield 75 mg (97%) colourless crystals with a melting point of 208–210° C.

The product (dissolved in $(D_6)$DMSO) is characterized by the following signals in the $^1$H-NMR spectrum (results for δ in ppm): 12.4 (br. NH); 8.31 (s, H—C(8); 8.07 (s, H—C(2); 6.24 (dd, J=8.8, 1.6 Hz, H—C(1'); 5.45 (d, J=4.0 Hz, 3'-OH); 4.70 (m, 5'-OH); 4.36 (m, J=3.5 Hz, H—C(3'); 3.92 (m, H—C(4'); 3.71 and 3.60 (2 m, H$_2$—C(5'); 2.76 (m, H$_α$—C(2'); 2.25 (d, J=−15 Hz, H$_β$—C(2').

$^{13}$C-NMR ($(D_6)$DMSO): 156.7 (C-6); 147.8 (C-4); 145.9 (C-2); 139.1 (C-8); 124.0 (C-5); 85.6 (C-4'); 82.6 (C-1'); 69.1 (C-3'); 59.9 (C-5'); 41.1 (C-2').

The UV spectrum (in MeOH) exhibits an absorbance maximum at 249 nm ($ε_{max}$=10500).

Elemental analysis: calculated: C, 47.62; H, 4.80; N, 22.21. found: C, 47.76; H, 4.98; N, 22.15.

EXAMPLE 6

9-[2'-deoxy-5'-O-(4,4'-dimethoxytriphenylmethyl)-β-D-xylopentofuranosyl]-6-[[(dimethylamino)-methylidene]amino]adenine A solution of 2'-deoxy-xyloadenosine (502 mg, 2 mmol) in dimethylformamide (10 ml) was stirred for 18 h with dimethylformamide-diethylacetal (1.7 ml, 10 mmol) at room temperature and subsequently concentrated by evaporation [TLC (silica gel, CH$_2$Cl$_2$-acetone-Et$_3$N (20:10:1)) R$_f$ 0.1]. The oily residue (0.8 g) was dissolved without further purification in pyridine (50 ml) and concentrated to half its volume. After addition of 4,4'-dimethoxytriphenylmethyl chloride (760 mg, 2.24 mmol) and ethyldiisopropylamine (0.37 ml, 2.1 mmol), it was stirred for 3.5 h at room temperature. After removing pyridine by evaporation and re-steaming with toluene (2×30 ml), the residue was dissolved in CH$_2$Cl$_2$-acetone-Et$_3$N (20:10:1, v/v/v, 5 ml) and chromatographed on silica gel 60 (6×10 cm, 0.5 bar; mobile solvent: CH$_2$Cl$_2$-acetone-Et$_3$N, 20:10:1). Yield: 520 mg (43%) colourless foam.

TLC (silica gel, CH$_2$Cl$_2$-acetone, Et$_3$N 20:10:1) Rf 0.48.

The product (dissolved in $(D_6)$DMSO) is characterized by the following signals in the $^1$H-NMR spectrum (results for δ in ppm): 8.93 (s, =CH—); 8.43 (s, H—C(8) ); 8.34 (s, H—C(2)); 7.17–7.40 (m, DMT); 6.75–6.84 (m, DMT); 6.41 (m, H—C(1')); 5.75 (d, J=5.0 Hz, 3'-OH); 4.33 (m, H—C (3')); 4.20 (m, H—C(4')); 3.7 (m, 2 CH$_3$ and H$_2$—C(5)); 3.20 and 3.13 (2 s, 2 OCH$_3$); 2.78 (m, H$_α$—C(2')); 2.3 (d, H$_β$—C(2')).

Elemental analysis: calculated: C, 67.09; H, 5.96; N, 13.81. found: C, 66.89; H, 6.03; N, 13.64.

EXAMPLE 6a

9-(2'-deoxy-β-D-threo-pentofuranosyl)N$^6$-benzoyladenine

2'-deoxy-xyloadenosine (100 mg, 0.40 mmol) is suspended in dry pyridine (10 ml) and evaporated to a third of its volume. Trimethylchlorosilane (0.25 ml, 2 mmol) is added and it is allowed to stir for 15 minutes at room temperature. Subsequently benzoyl chloride (0.23 ml, 2 mmol) is added and it is stirred for a further 2 hours at room temperature. After cooling to 0° C. and adding 0.5 ml H$_2$O, 25% aqueous ammonia is added after a further 5 minutes and it is stirred for a further 30 minutes at room temperature. After evaporating the pyridine, the residue is dissolved in water and extracted with ethyl acetate (10 ml). The organic phase is concentrated by evaporation and admixed with pyridine (3 ml) and 25% aqueous ammonia (1 ml). After one hour, it is concentrated by evaporation and chromatographed on silica gel 60 (70 ml) using the mobile solvent ethyl acetate/acetone/ethanol H$_2$O (18:3:2:2) during which a main product is eluted. The yield is 25 mg (60%), the melting point is 175–177° C.

TLC (silica gel, ethyl acetate/acetone/ethanol/H$_2$O, 18:3:2:2): R$_f$ 0.4.

The product (dissolved in $(D_6)$DMSO) is characterized by the following signals in the $^1$H-NMR spectrum (results for δ in ppm): 11.2 (br, NH); 8.77 (s, H—C(8)); 8.70 (s, H—C(2)); 8.05 and 7.60 (2 m, benzoyl-H); 6.47 (d, H—C (1')); 5.55 (d, 3'-OH); 4.73 (t, 5'-OH); 4.42 (m, H—C(3')); 4.00 (m, H—C(4')); 3.74 (m, H$_2$—C(5')); 2.83 (m, H$_α$—C (2')); 2.38 (m, H$_β$—C(2')).

Elemental analysis: calculated: C, 57.46; H, 4.82; N, 19.71. found: C, 57.36; H, 4.95; N, 19.64.

EXAMPLE 6b

9-[2'-deoxy-5'-O-(4,4'-dimethoxytriphenyl)-β-D-threo-pentofuranosyl]-N$^6$-benzoyl-adenine N$^{Bz}$dxA (280 mg, 0.79 mmol) is dried by evaporating with pyridine (30 ml) and the residue is dissolved in pyridine (15 ml). 4,4'-dimethoxytriphenylmethyl chloride (315 mg, 0.93 mmol) and ethyl diisopropylamine (0.14 ml, 0.85 mmol) are added to this and stirred for 3 hours at room temperature. Subsequently it is concentrated by evaporation and re-vapourized several times with toluene (50 ml).

The residue is eluted on silica gel 60 (60 ml) with CH$_2$Cl$_2$/acetone (12:5) to obtain a main zone from which 428 mg (82%) of the title compound is obtained as a colourless foam after removing the solvent by evaporation.

TLC (CH$_2$Cl$_2$/acetone, 12:5): R$_f$ 0.47.

The product (dissolved in $(D_6)$DMSO) is characterized by the following signals in the $^1$H-NMR spectrum (results for δ in ppm): 11.2 (br. NH); 8.77 (s, H—C(2)); 8.07–6.77 (m, benzoyl- and DMT-H); 6.53 (d, H—C(1')); 5.51 (d, 3'-OH); 4.37 (m, H—C(3')); 4.28 (m, H—C(4')); 3.72 (m, 2 OCH and H$_2$—C(5')); 2.79 (m, H$_α$—C(2')); ca. 2.5 (m, H$_β$—C (2')):

Elemental analysis: calculated: C, 69.39; H, 5.36; N, 10.65. found: C, 69.48; H, 5.84; N, 10.51.

EXAMPLE 7

9-[2'-deoxy-5'-O-(4,4'-dimethoxytriphenylmethyl)-β-D-xylopentofuranosyl]-6-[[(dimethylamino) methylidene]amino]adenine-3'(H-phosphonate) triethylammonium salt 1,2,4-triazole (0.94 g, 13.6 mmol) is added to a solution of PCl$_3$ (360 μl, 4.1 mmol) and N-methylmorpholine (4.5 ml, 41 mmol) in CH$_2$Cl$_2$ (35 ml) and the reaction mixture is stirred for 30 min at room temperature. After cooling to 0° C., a solution of the protected nucleoside from example 6

(480 mg, 0.79 mmol) in $CH_2Cl_2$ (10 ml) is added dropwise and the solution is stirred for 10 min at room temperature. Subsequently the reaction mixture is poured into triethylammonium bicarbonate buffer (1 M, pH 8, 50 ml), the phases are separated and the aqueous phase is extracted twice with $CH_2Cl_2$ (30 ml). The combined organic phases are dried over $Na_2SO_4$ and concentrated by evaporation. The residue is chromatographed on silica gel 60 (6×10 cm, 0.5 bar, mobile solvent: 600 ml $CH_2Cl_2$—$Et_3N$, 92:8; $CH_2Cl_2$—MeOH—$Et_3N$, 88:10:2). After concentrating the main zone by evaporation, the residue is dissolved in $CH_2Cl_2$ (15 ml) and extracted twice with $Et_3NH^+HCO_3^-$ (1 M, pH 8, 20 ml). The organic phase is dried over $Na_2SO_4$ and concentrated by evaporation; yield 390 mg (64%) colourless foam.

TLC (silica gel, $CH_2Cl_2$—MeOH—$Et_3N$, 88:10:2): $R_f$ 0.65.

The product (dissolved in $(D_6)DMSO$) is characterized by the following signals in the $^1H$-NMR spectrum (results for $\delta$ in ppm): 10.5 (s, br, NH); 8.95 (s, =CH—); 8.45 (s, H—C(8)); 8.41 (s, H—C(2)); 7.39–6.75 (m, DMT); 6.79 and 5.29 (P—H); 6.45 (m, H—C(1')); 4.79 (H—C(3')); 4.28 (m, H—C(4')); 3.71 (m, 2 $CH_3$ and $H_2$—C(5)); 3.20 and 3.13 (2 s, 2 $OCH_3$); 2.96 (m, $CH_2$); 2.5 (m, $H_2$—C(2')); 1.10 (t, $CH_3$).

Elemental analysis: calculated: C, 62.08; H, 6.77; N, 12.67. found: C, 62.12; H, 6.90; N, 12.46.

EXAMPLE 7a

9-[2'-deoxy-5'-O-(4,4'-dimethoxytriphenylmethyl)-β-D-threo-pentofuranosyl]-$N^6$-benzoyladenine-3'-(H-phosphonate)triethylammonium salt 1,2,4-triazole (359 mg, 5.2 mmol) is added to a solution of $PCl_3$ (136 µl, 1.56 mmol) and N-methylmorpholine (1.72 ml, 15.6 mmol) in $CH_2Cl_2$ (13 ml). The solution is stirred for 30 min at room temperature, subsequently cooled to 0° C., and the completely protected nucleoside (DMT-$N^{Bz}$dxA, 200 mg, 0.3 mmol, dissolved in $CH_2Cl_2$ (8 ml)) is added. After stirring for 30 min at room temperature, the solution is poured into 1 mol/l TBK buffer (pH 8, 20 ml) and the organic phase is separated. After extracting the aqueous phase again with dichloromethane (30 ml), the combined organic phases are dried over $Na_2SO_4$ and concentrated by evaporation. The residue is chromatographed on silica gel 60 (50 ml). 31 mg (16%) of the starting material is eluted with $CH_2Cl_2$-triethylamine (92:8); the desired H-phosphonate is eluted with $CH_2Cl_2$-methanol-triethylamine (88:5:2). After withdrawing the solvent, the residue is dissolved in $CH_2Cl_2$ (30 ml) and extracted with 1 mol/l TBK buffer (pH 8, 30 ml). After drying the organic phase over $Na_2SO_4$, it is concentrated by evaporation. 158 mg (64%) of a colourless foam is obtained.

TLC (silica gel, $CH_2Cl_2$—MeOH—$Et_3N$, 88:5:2): $R_f$ 0.3.

$^{31}$P-NMR $((D_6)DMSO)$: 1.37 ppm ($^1J(P—H)$=594 Hz; $^3J(P—H-3')$=8.7 Hz).

Elemental analysis: calculated: C, 64.22; H, 6.25; N, 10.21. found: C, 64.47; H, 6.48; N, 10.51.

EXAMPLE 8

9-[2'-deoxy-5'-O-(4,4'-dimethoxytriphenylmethyl)-β-D-xlopentofuranosyl]-6-[[(dimethylamino)methylidene]amino]adenine-3'-[2-(cyanoethyl)-N,N-diisopropyl-phosphoramidite]

Ethyl diisopropylamine (110 µl, 0.63 mmol) is added to a solution of the protected nucleoside from example 6 (122 mg, 0.2 mmol) in dry THF (1.5 ml). Subsequently chloro-β-cyanoethyloxy-(N,N-diisopropylamino)phosphane (50 µl, 0.22 mmol) is added dropwise within 2 minutes under $N_2$. After the reaction mixture has been stirred for 30 minutes at room temperature, aqueous $NaHCO_3$ (5%, 4 ml) is added and extracted twice with $CH_2Cl_2$ (5 ml). The combined organic phases are dried over $Na_2SO_4$, concentrated by evaporation and the residue is chromatographed on silica gel 60H (3×6 cm, 0.5 bar, mobile solvent: $CH_2Cl_2$—EtOAc—$Et_3N$, 45:45:10); yield: 156 mg (96%) colourless oil.

TLC (silica gel, $CH_2Cl_2$—EtOAc—$Et_3N$, 45:45:10) $R_f$ 0.50 and 0.53 (2 diastereoisomers).

$^{31}$P-NMR $((D_6)DMSO)$: 151.5, 146.7 ppm.

EXAMPLE 9

1-[2'-deoxy-5'-O-(4,4'-dimethoxytriphenylmethyl)-3'-O-succinyl-β-D-threo-pentofuranosyl]-thymine 70 mg 4-dimethylaminopyridine (0.54 mmol) and 230 mg succinic anhydride (2.3 mmol) are added to a solution of 250 mg of the nucleoside from example 2 (0.46 mmol) in 10 ml dry pyridine and the mixture is stirred for 70 hours at 40° C. Afterwards 3 ml water is added to the reaction mixture and it is evaporated to a dry residue. Traces of pyridine are removed by co-evaporation with toluene. The remaining oil is dissolved in $CH_2Cl_2$ and extracted by shaking successively with 10% aqueous citric acid and water. The organic phase is dried over sodium sulfate and concentrated by evaporation. The residue is taken up in 2 ml of a mixture of $CH_2Cl_2$ and pyridine (95:5) and the solution is slowly poured into 50 ml of a mixture of n-pentane/ether (1:1) while stirring. The precipitate which comes down is filtered and purified by means of flash chromatography on silica gel 60 (column: 10×6 cm, acetonitrile-water (9:1)). The desired compound (180 mg, 61% of theoretical yield) is obtained as the main fraction in the form of a colourless powder.

TLC (silica gel, acetonitrile-water, 9:1) $R_f$ 0.8.

The product is characterized by the following signals in $^{13}$C-NMR (solution in $(D_6)DMSO$) (results in ppm): 173.6, 171.2 (2 C=O); 163.8 (C-6); 158.3 (DMT); 150.5 (C-2); 144.7 (DMT); 135.5 (C-4); 135.4–126.9 (10 signals, DMT); 113.3 (quart.-C, DMT), 109.0 (C-5); 85.8 (DMT); 83.6 (C-4'); 80.6 (C-1'); 72.3 (C-3'); 61.2 (C-5'); 55.1 ($OCH_3$, DMT); 40.6 (C-2'); 29.1, 29.0 (2 $CH_2$); 12.3 ($CH_3$-thymine).

EXAMPLE 10

Fractosil-bound 1-[2'-deoxy-5'-O-(4,4'-dimethoxytriphenylmethyl)-3'-O-succinyl-β-D-threo-pentofuranosyl]-thymine 40 mg 4-nitrophenol (0.29 mmol) and 60 mg N,N-dicyclohexylcarbodiimide (0.3 mmol) are added to a solution of 100 mg nucleoside from example 9 (0.16 mmol) in 1 ml of a mixture of dioxan-5% pyridine while stirring at room temperature. After 2 hours, the precipitated dicyclohexylurea is removed by filtration and 200 mg Fractosil® 200 (Merck, 450 µEq. $NH_2$/g) and 1 ml dimethyldormamide are added to the filtrate. After addition of 0.2 ml triethylamine, the suspension is shaken for 4 hours at room temperature. Then 60 µl acetic anhydride is added and the shaking is continued for a further 30 minutes. Afterwards the nucleoside bound to the silica gel is filtered off, washed with dimethylformamide, ethanol and ether and dried in a vacuum.

The amount of nucleoside bound to silica gel was determined as follows: 5 mg of the Fractosil support was treated with 10 ml 0.1 M 4-toluenesulfonic acid in acetonitrile. The supernatant was measured spectrophotometrically at 498 nm during which 50.4 µmol nucleoside per g Fractosil was found ($\epsilon_{DMT}$=70000).

EXAMPLE 10a

Fractosil-bound 9-[2'-deoxy-5'-O-(4,4'-dimethoxytriphenylmethyl)-β-D-xylopentofuranosol]-6-[[dimethylamino)methylidene]amino]adenine N,N-dimethylaminopyridine (60 mg, 0.49 mmol) and succinic anhydride (200 mg, 2 mmol) are added to a solution of the completely protected nucleoside from example 6 (250 mg, 0.41 mmol) in pyridine (10 ml) and the solution is stirred for 72 hours at 40° C. After addition of water (3 ml) it is evaporated to dryness and the residue is re-vapourized with toluene (50 ml). It is dissolved in $CH_2Cl_2$ and extracted with 10% aqueous citric acid solution (30 ml) and water (30 ml). The organic phase is dried over $Na_2SO_4$ and concentrated by evaporation. 278 mg (96%) of a colourless material is obtained which is reacted without further purification. The succinate (142 mg, 0.20 mmol) is dissolved in a 5% solution of pyridine in dioxane (1.25 ml) and admixed with p-nitrophenol (50 mg, 0.36 mmol) and dicyclohexylcarbodiimide (80 mg, 0.40 mmol) at room temperature. It is allowed to stir for 3 hours at this temperature and subsequently the precipitated dicyclohexylurea is filtered off. Subsequently dimethylformamide (1.25 ml) and Fractosil 200 (450 µeq $NH_2$/g) are added. After addition of triethylamine (250 µl), the suspension is shaken for 4 hours at room temperature and subsequently acetic anhydride (75 µl) is added. The shaking is continued for 30 minutes, the nucleoside bound to the silica gel is filtered off, washed with dimethylformamide, ethanol and ether and dried in a vacuum. The method described in example 10 was used to determined the nucleoside bound to the silica gel; the concentration of the nucleoside bound to the silica gel is 27 µmol/g Fractosil.

EXAMPLE 11

Solid Phase Synthesis of the Oligonucleotide d($xT_{12}$)

The synthesis of the oligomer was carried out on a 1 µmol scale using the 3'-hydrogenphosphonate from example 3. The synthesis followed the standard protocol of the DNA synthesizer for the 3'-H-phosphonate method (Applied Biosystems Users Manual for the DNA Synthesizer 380 B).

The 4,4'-dimethoxytrityl protecting group of the oligomer was removed by treatment with 80% acetic acid for 5 minutes at room temperature. It was purified by HPLC on a RP-18 column and a gradient system of 0.1 M $Et_3NHOHAc$ pH 7/acetonitrile (95:5) [A] and acetonitrile [B]. The pure oligomer was desalted on a 4×25 mm HPLC cartridge (RP-18 silica gel) and subsequently lyophilized.

EXAMPLE 11a

Solid Phase Synthesis of the Oligonucleotide d (GTAGxAxAxCTAC)

The synthesis of the oligonucleotide was carried out on a 1 µM scale using the nucleoside-3'-O-(2-cyanoethyl)-N,N-diisopropylamino-phosphoramidites of the bases A, G, C and T as well as the corresponding phosphoramidites of the 3'-xylo-nucleosides xT and xA from examples 4 and 8. The synthesis followed the standard protocol of the DNA synthesizer for the phosphoramidite method (Applied Biosystems Users Manual for the DNA synthesizer 380 B). The $NH_2$ protecting groups were cleaved with 25% aqueous ammonia solution at 60° C. for 48 hours. The removal of the 5'-O-dimethoxytrityl protecting groups, the purification by HPLC and the desalting were carried out as described in example 11.

EXAMPLE 12

Solid Phase Synthesis of Further Oligonucleotides

The solid phase synthesis of the oligomers d(xTCG xTCG CxTG xTCxT CCG CxTxT CxTxT CCxT GCC xA) and d(GxTxAGAATTCxTxAC) was carried out in an anlogous manner to that described in example 11.

EXAMPLE 12a

Figure 2:
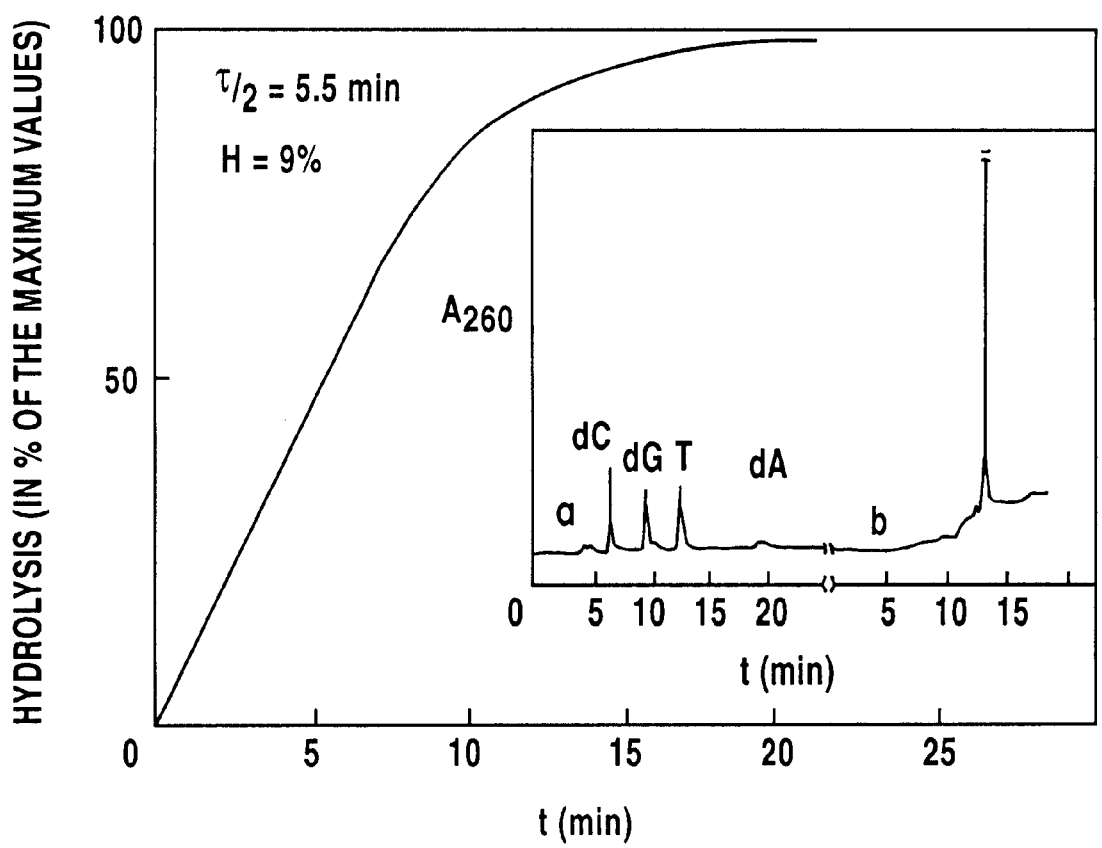

Phosphodiesterase Cleavage of the Oligomer d (GTAGAAxTxTCTAC) (FIG. 2)

0.2 $A_{260}$ units of the oligonucleotide was dissolved in 200 µl 0.1 M Tris-HCl buffer (pH 8.3) and treated for 45 minutes at 37° C. with 12 µg calf spleen phosphodiesterase (Boehringer Mannheim, Catalogue No. 108 251) and subsequently for 30 minutes at 37° C. with 2 µg alkaline phosphatase (Boehringer Mannheim, Catalogue No. 108 154).

Afterwards the reaction mixture was analyzed by HPLC (RP-18, eluting agent 0.1 M ($Et_3NH$)OAc (pH 7)/acetonitrile (95:5) [A], followed by 0–20% acetonitrile [B] in [A], flow rate ca. 1 ml/min.).

It turns out that the oligomer is only partially hydrolyzed; afterwards the phosphodiesterase only cleaves off the non-modified 5'-terminal nucleotides with a t/2 value of 5.5 min. (hypochromicity of the final product 9%, $T_M$=36° C.). As the HPLC profile (inserted figure) shows, the major portion of the oligonucleotide is present in an unchanged form.

EXAMPLE 12b

Phosphodiesterase Cleavage of the Oligomer d (GxTxAGAATTCxTxAC)

The cleavage of this oligonucleotide by calf spleen phosphodiesterase was examined in an analogous manner to that set forth in example 12a. In this case only a very slow and negligible hydrolysis is observed (hypochromicity of the final product 3%, $T_M$=27° C.).

EXAMPLE 13

Hybridization Complex d($xT_{12}$) with d($A_{12}$)
a) Melting Curves

Figure 3:
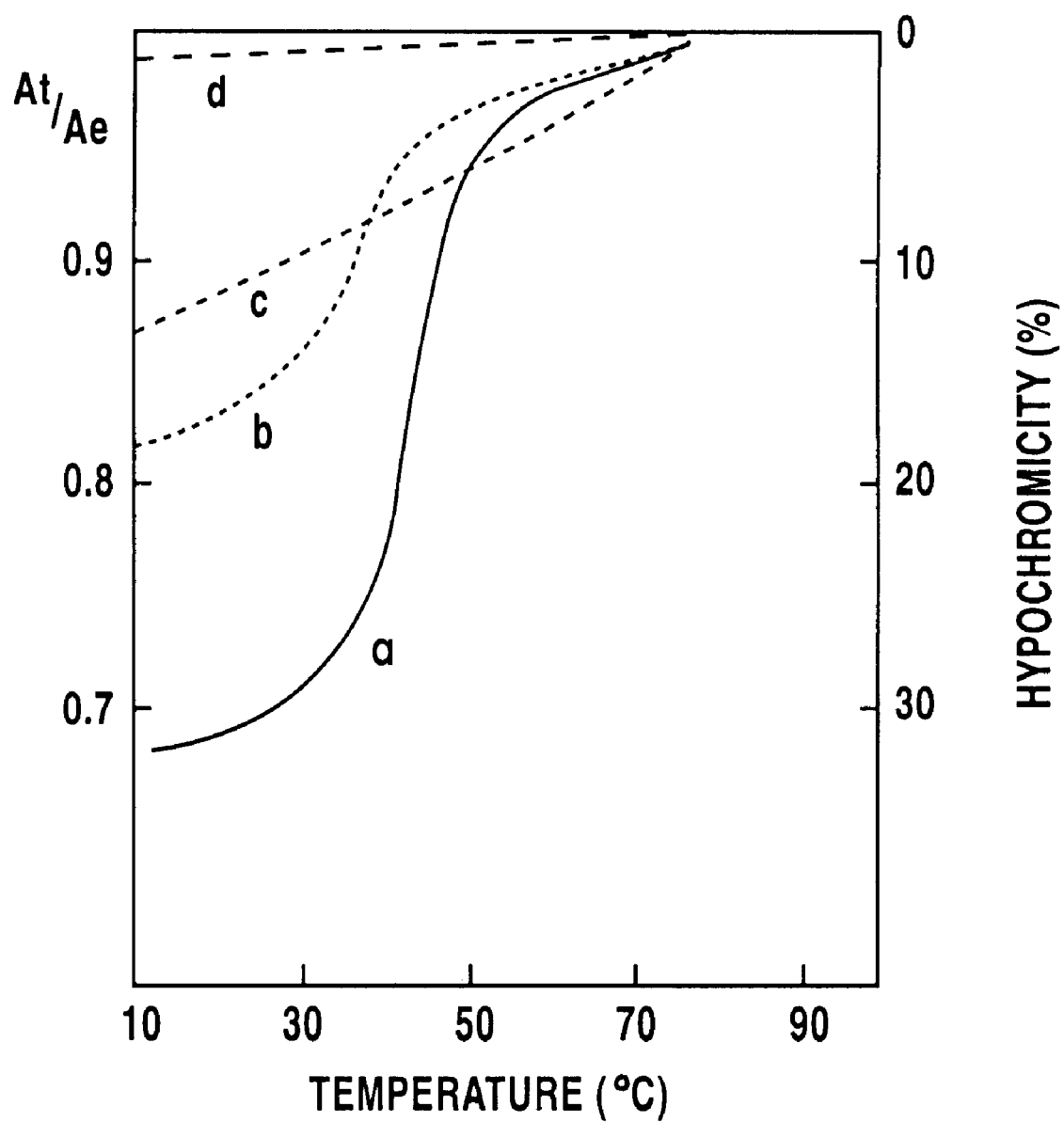
FIG. 3 shows the melting curve of the d($A_{12}$)/d (x$T_{12}$) hybrid (b) in comparison to hybrid d($A_{12}$)/d($T_{12}$) (a) and of the single-stranded oligonucleotides d($A_{12}$) (c) and d($T_{12}$) (d).

2 µmol of each of the oligonucleotides was used for this. The measurement was carried out in a thermostatically controlled cell using a Shimadzu 210-A UV spectrophotometer in conjunction with a "Kipp und Zonen BD 90" recorder. The increase in UV absorbance at either 260 or 284 nm was recorded as a function of time while the temperature of the solution was increased linearly (10–80° C.) by 20°/hour (Lauda PM-350 programmer combined with a Lauda RCS 6 bath with R 22 unit). The respective temperature was measured in the reference cell using a Pt resistor. The hypochromicity values were calculated from the initial and final absorbance. The melting curves obtained in this way are shown in FIG. 3. Those for the hybrid d($A_{12}$)/d($xT_{12}$) (b)

have a shape which is characteristic for a cooperative melting of double strands (cf. curve (a) for d($A_{12}$)/d($T_{12}$)) which is not exhibited by the single-stranded homopolymers (d$CA_{12}$) (c) and d($T_{12}$) (d).

b) CD Spectroscopy (FIG. 3)

Figure 4:
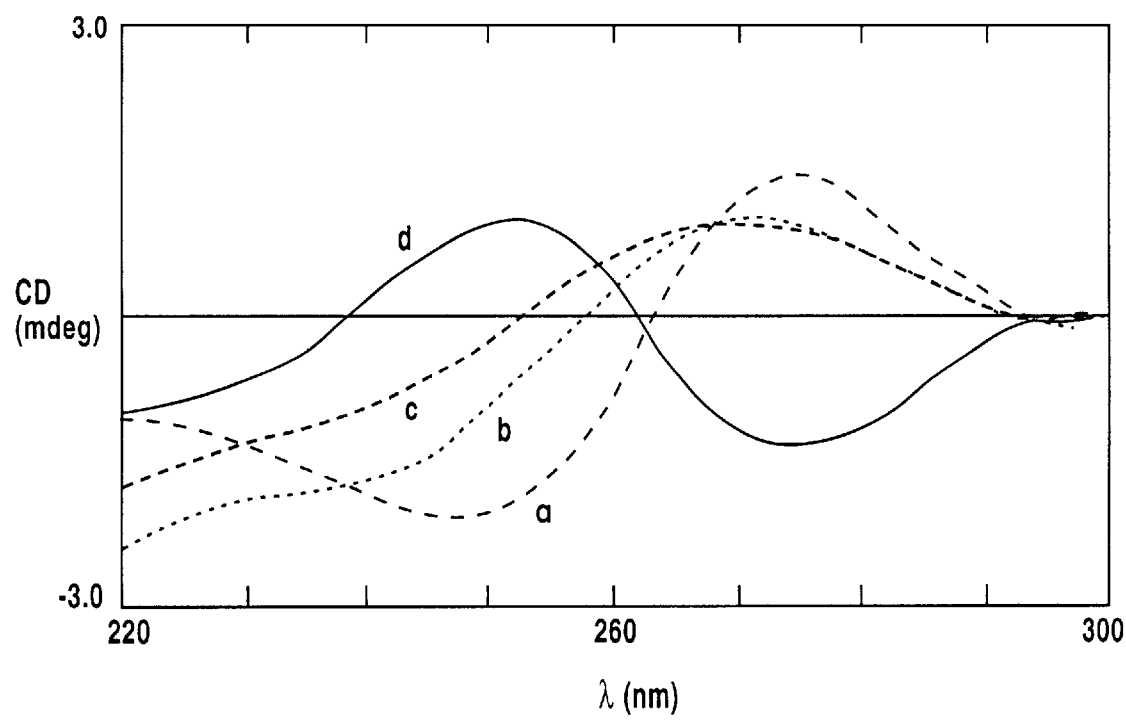
FIG. 4 shows the CD spectrum of d ($T_{12}$) (a), T (b), xT (c) and d (x$T_{12}$) (d).
Figure 5:
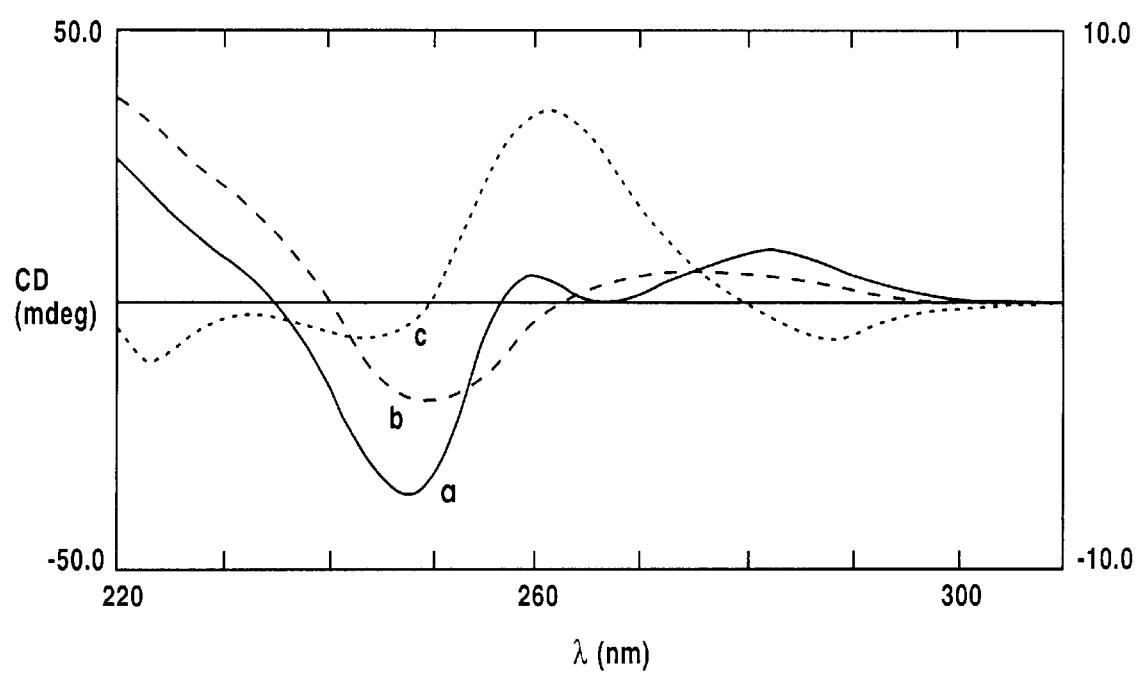
FIG. 5 shows the CD spectrum of the hybrids d($A_{12}$)/d ($T_{12}$) (a) and d($A_{12}$)/d(x$T_{12}$) (c) as well as of the single-stranded oligonucleotide d($A_{12}$) (b).

2 μmol of each of the respective single strands (d$A_{12}$) and d($T_{12}$) or d(x$T_{12}$) were hybridized (60 mM cacodylate buffer pH 7.0, 1 M NaCl, 100 mM $MgCl_2$, 8° C.). A CD spectrum of the hybrids obtained as well as of the single strands d($T_{12}$), d(x$T_{12}$) and d($A_{12}$) and of the monomers T and xT was recorded on a Jasco 600 spectropolarimeter with a thermally controlled (Lauda RCS 6) 1 cm cuvette. The spectra obtained are shown in FIGS. 4 and 5.

It is appparent that the CD spectra of the hybrids differ clearly from the sums and differences of the single strands. This shows that a new type of double-stranded hybrid structure is formed.

EXAMPLE 14

Determination of Viral Gene Expression of HIV-I Infected H 9 Cells

Chronically infected H 9 (ATCC CRL 8543) cells were cultured in the presence of various concentrations of the oligomer d(xTCG xTCG CxTG xTCxT CCG CxTxT CxTxT CCxT GCC xA) from example 12 in 200 μl culture medium (RPMI 1640 containing 15% foetal calf serum, 4 mmol L-glutamine, 50 nmol 2-mercaptoethanol, 50 units penicillin and 50 μg streptomycin/ml). After 6 days culture, 100 μl of the culture supernatant was removed and the amount of p24 gag protein was determined by means of radioimmunoassay.

Whereas in the control experiment (without oligomer) the amount of p24 gag protein increased within 5 days to values around 200 ng/ml, protein synthesis when using the oligomer was 50 ng/ml to ca. 5 ng/ml depending on the dose.

EXAMPLE 15

2,6 Diamino-9-(μ-D-ribofuranosyl)purine (2) [1]

5.66 g (20 mmol) guanosine (1) (dried at 80° C./$P_2O_5$) is sylylated by heating for 10 hours to 140° C. with 200 ml hexamethyldisilazane (HMDS) and 0.5 ml trimethylchlorosilane (TCS); excess HMDS is subsequently removed at normal pressure by distillation and the remaining viscous syrup is transferred with a mixture of 35 ml absolute toluene and 2 ml HMDS into a 100 ml autoclave. After addition of 4 ml of a 0.5 M solution (2 mmol) of trimethylsilyl triflate (($CH_3$)$SiSO_3CF_3$) in benzene, a pressure of 5 atm $NH_3$ is applied at +5° C. for 30 min; the autoclave is then heated for 48 h to 150° C. After carefully discharging the ammonia, the content of the autoclave is washed out with 150 ml methanol and, after addition of 150 ml water, heated for 4 h on a steam bath. After removing the methanol, it is diluted with water to 250 ml, the boiling solution is decolourized with a small amount of active charcoal and filtered during which it is rewashed with 100 ml hot water. After concentration to 250 ml, the yellow filtrate crystallizes slowly on cooling and standing at 24° C. After filtration and further evaporation of the mother liquor to 100 ml, 4.23 g (75.5%) colourless crystals of 2 [1] is obtained.

TLC (silica gel, mobile solvent EtOAc—MeOH; 60:40, Rf=0.55)

EXAMPLE 15

2,6-Diamino-9-(2-O-p-toluenesulfonyl-β-D-ribofuranosyl)purine (3) [2]

2.40 g (2) and 2.2 g dibutyl-tin oxide are suspended in 200 ml MeOH and boiled for 2 h under reflux during which a clear solution is slowly formed. After cooling to room temperature and addition of 18 ml triethylamine, 24 g p-toluenesulfonic acid chloride is slowly added and subsequently it is stirred for a further 15 min. Excess solvent is withdrawn at 40° C. and the residue is taken up with 200 ml water. After extraction with ether (2×100 ml), the aqueous phase is evaporated to 100 ml and stored overnight at 0° C. The crude product which precipitates in this process is collected and purified by column chromatography (silica gel, mobile solvent B). The mother liquor is evaporated to dryness, adsorbed onto silica gel and also chromatographed. 2.85 g (77%) of compound (3) [2] is obtained. F.p.=134° C.; TLC (silica gel, mobile solvent EtOAc—MeOH, 85:15) Rf=0.45; 1H-NMR ([D6]DMSO): 7.82 (s, H—C(8)); 6.83 (s, NH2); 5.91 (d, J(H—C(1'), H—C(2')=7.5 Hz; H—C(1')); 5.67 (s, NH2); 5.41 (m, $H_\alpha$—C(2')); 4.29 (m, H—C(3')); 4.01 (H—C(4')); 3.55 (m, CH2); 3.17 (d, $H_\beta$—C(C2')); 2.29 (s, —CH3).

EXAMPLE 16

2'-amino-(2'-deoxy-β-D-threo-pentofuranosyl) adenine (4) [2]

A 1 M solution of Li$Et_3$BH in THF (34 ml) is added to a solution of (3) (1.4 g; 2.75 mmol) in 30 ml dry DMSO under an argon atmosphere. The resulting colourless solution is stirred overnight at room temperature and 7 ml water is added dropwise over a period of 30 min. Subsequently the solvent is withdrawn and the residue is desalted on a Dowex 1×2 ($OH^-$) column (4×30 cm) with 500 ml water. The reaction product can now be eluted from the column with a MeOH/water mixture (1:1) and after evaporation the appropriate fractions can be obtained. Recrystallization from water (100 ml) yields 760 mg (98%) pure (4) [3]. F.p.=175° C.; 1H-NMR (([D6]DMSO): 7.95 (s, H—C(8)); 6.78 (s, NH2); 6.07 (d, H—C(1')); 5.81 (s, NH2); 4.65 (m, OH—C (5')); 4.30 (br, H—C(3')); 3.84 (m, H—C(4')); 3.72 (m, CH2-C(5')); 2.73 (m, $H_\alpha$—C(2')); 2.23 (d, J($H_\alpha$—C(2'), $H_\beta$—C(2'))=−14.5 Hz; $H_\beta$—C(2')).

EXAMPLE 17

(2'-deoxy-β-D-threo-pentofuranosyl)guanine (5)

Compound (4) is dissolved in 100 ml water while heating and, after cooling to ca. 30° C., adenosine deaminase (200 μl) is added. After the reaction mixture has been stirred overnight at 30° C., the reaction course is monitored by means of TLC and UV spectroscopy. After withdrawing the solvent, the reaction product is evaporated several times with acetone and finally 650 mg (92%) (5) is obtained. F.p.>250° C.; TLC (silica gel, mobile solvent iPrOH-25%$NH_3$aq-$H_2O$; 3:1:1): $R_f$=0.61. 1H-NMR ([D6]DMSO): 7.95 (s, H—C(8)); 6.49 (s, NH2); 6.05 (d, H—C(1')); 5.43 (s, OH—C(3')); 4.67 (s, OH—C(5')); 4.33 (d, H—C(3')); 3.87 (s, H—C(4')); 3.65 (m, CH2-C(5')); 2.70 (m, $H_\alpha$—C (2')); 2.20 (d, $H_\beta$—C(2')).

EXAMPLE 18

N2,3',5'-triisobutyryl-(2'-deoxy-β-D-threo-pentofuranosyl)guanine (6)

500 mg (5) is dried by evaporating several times with absolute pyridine and dissolved in 20 ml pyridine while heating gently. After cooling to 0° C. in an ice bath, 1.95 ml (18.5 mmol) isobutyryl chloride is added slowly under nitrogen while stirring vigorously. The turbid, gelatinous reaction mixture is stirred for a further 1 hour at room temperature and subsequently hydrolyzed with a solution of 2.5 g NaHCO$_3$ in 40 ml H$_2$O. After concentrating the solution to ca. 20 ml and allowing it to stand at 0° C. overnight, the reaction product is aspirated and re-washed with 20 ml ether. After column chromatography using silica gel (5 cm×30 cm), mobile solvent CHCl$_3$—MeOH; 8:2, 820 mg amorphous (6) [4] is obtained. F.p.=91° C., TLC (mobile solvent CHCl$_3$—MeOH; 8:2) R$_f$=0.40: 1H-NMR ([D6] DMSO): 12.05 (br, NH); 11.70 (br, NH); 8.14 (s, H—C(8)); 6.14 (d, H—C(1')); 5.30 (s, OH—C(3')); 4.68 (s, OH—C(5')); 4.36 (s, H—C(3')); 3.94 (m, H—C(4')); 3.72 (m, CH2-C(5')); 2.77 (m, H$_\alpha$—C(2')); 2.28 (d, H$_\beta$—C(2')); 1.13 (m, 7H-ibut.); C$_{22}$H$_{31}$N$_5$O$_7$ (477.51): calc.: C, 55.34; H, 6.54; N, 14.67. found: C, 55.18; H, 6.57; N, 14.73.

EXAMPLE 19

N2-isobutyryl-(2'-deoxy-β-D-threo-pentofuranosyl) guanine (7)

1.2 g (2.5 mmol) (6) is dissolved in 40 ml MeOH and cooled to 0° C. in an ice bath. Subsequently 1 N aqueous NaOH solution is added in portions until the pH value increases to 12. After 50 min, the reaction is stopped by addition of ion exchanger (Dowex W×8; pyridinium form) and the neutral solution is filtered. After washing the resin with MeOH, the solvent is withdrawn and the residue is re-crystallized from a very small amount of water. After completing the crystallization by allowing it to stand overnight in a refrigerator, 560 mg (72%) white needles of compound (7) is obtained. F.p.>260° C.; TLC (silica gel, mobile solvent CHCL$_3$—MeOH, 9:1) Rf=0.42; 1H-NMR ([D6]DMSO): 12.05 (br, NH); 11.70 (br, NH); 8.20 (S, H—C(8)); 6.14 (d, H—C(1')); 5.30 (s, OH—C(3')); 4.68 (s, OH—C(5')); 4.36 (s, H—C(3')); 3.94 (m, H—C(4')); 3.72 (m, CH2-C(5')); 2.77 (m, H$_\alpha$—C(2')); 2.28 (d, H$_\beta$—C(2')); 1.13 (m, 7H-i-but.); C$_{14}$H$_{19}$N$_5$O$_5$ (337.3): C, 49.85; H, 5.68; N, 20.67; found.: C, 49.98; H, 5.81; N, 20.75.

EXAMPLE 20

N2-isobutyryl-5'-O-dimethoxytrityl-(2'-deoxy-β-D-threo-pentofuranosyl)guanine (8)

300 mg (7) (0.89 mmol) is dried by evaporating several times with absolute pyridine and subsequently dissolved in 5 ml absolute pyridine. After addition of dimethylaminopyridine (16 mg, 0.13 mmol) 150 mg (0.4 mmol) 4',4'-dimethoxytrityl chloride is added under argon. After stirring for 4 hours at room temperature and subsequent addition of 45 ml 5% NaHCO$_3$ solution, it is extracted with CH$_2$Cl$_2$ (3×50 ml). The combined organic phases are dried over Na$_2$SO$_4$, filtered and the solvent is withdrawn. After chromatography on silica gel (20×5 cm, mobile solvent CHCl$_3$—MeOH, 8:2) and evaporation of the main zone, 423 mg (74%) amorphous (8) is obtained. TLC (silica gel, mobile solvent CHCl$_3$—MeOH, 8:2) Rf=0.38

1H-NMR ([D6]DMSO): 12.09 (br, NH); 11.77 (br, NH); 8.07 (s, H—C(8)); 6.22 (d, H—C(1')); 5.30 (s, OH—C(3')); 4.34 (s, H—C(3')); 4.21 (s, H—C(4')); 3.71 (s, 3H—OCH3); 3.20 (m, H—C(5')); 2.74 (m, H$_\alpha$—C(2')); 2.30 (m, H$_\beta$—C(2')); 1.12 (m, 7H-i-but.);

EXAMPLE 21

N2-isobutyryl-5'-dimethoxytrityl-(2'-deoxy-β-D-threo-pentofuranosyl)guanine 3'-phosphonate (9a)

The compound was prepared and processed as described for compound 16.

EXAMPLE 22

N2-isobutyryl-5'-dimethoxytrityl-(2'-deoxy-β-D-threo-pentofuranosyl)guanine 3'[(2-cyanoethyl)-N, N-diisopropylphosphoramidite [9b]

Compound 9b was prepared and processed as described in [6].

EXAMPLE 23

9-(2'-deoxy-β-D-threo-pentofuranosyl)guanine 3'-[3-(N-'Fractosil'carbamoyl)propanoate] [9c]

The compound 9c was prepared and processed as described in [6].

EXAMPLE 24

4-benzoylamino-1-(2'-deoxy-β-D-erythro-pentofuranosyl)-2(1H)-pyrimidinone (10)

Compound 10 was prepared as described by Ti et al.

EXAMPLE 25

O2,3'-anhydro-1-[2'-deoxy-5'-O-(4-methoxybenzoyl)-β-D-threo-pentofuranosyl)-4-benzoylcytosine (11) [3]

A solution of diisopropylazodicarboxylate (DIAD, 3 ml, 15 mmol) and p-methoxybenzoic acid (2.3 g, 15 mmol) in dry DMF (11 ml) is added dropwise to a solution of (10) (3.3 g, 10 mmol) and PPh$_3$ (4 g, 15 mmol) in dry DMF (20 ml) within 5 minutes. The reaction mixture is allowed to stir for 15 min at room temperature and subsequently admixed with the same amount triphenylphosphine and DIAD. It is allowed to stir for a further 30 minutes at room temperature. Subsequently the solution is poured into ice-cooled Et$_2$O (250 ml) and the suspension which is obtained is cooled for 2 h. The white residue is filtered off and washed with Et$_2$O. Compound (11) is obtained by re-crystallization from ethanol as colourless platelets (3.42 g, 76%) melting point 188° C., Rf (CH$_2$Cl$_2$/CH$_3$OH): 0.38. UV ((MeOH): λmax (ε)= 318, 254 (30440, 17150). 1H-NMR [(D6)-DMSO]: 2.59–2.71 (m, Jgem=12.5 Hz, 2H, H-2'β, H-2'α); 4.41 (m, 2H, H-5'); 4.58 (m, 1H, H-4'); 5.47 (m, 1H, H-3'); 6.00 (m, 1H, H-1'); 6.52 (d, J5,6=7.25 Hz, 1H, H-5); 7.01, 7.84 (AB, q, 4H, C6H4); 7.68 (d, 1H, H-6); 7.45, 7.95 (m, 5H, arom. H). C$_{24}$H$_{21}$N$_3$O$_7$ (447.4): calc: C, 64.44; H, 4.73; N, 9.39. found: C, 64.49; H, 4.71; N, 9.31.

EXAMPLE 26

4-amino1-1-(2'-deoxy-β-D-threo-pentofuranosyl)-2 (1H)-pyrimidinone (12)

A solution of (11) (2.0 g, 4.5 mmol) dissolved in ethanol/water (1:1, 250 ml) is admixed with Dowex ion exchanger (OH-form; 250 ml, suspended in water). It is allowed to stir for 16 h at 50° C. The ion exchanger is filtered off and washed intensively with water. The filtrate and slurry are concentrated by evaporation, the oily residue is taken up in a small amount of methanol/ethyl acetate (1:1, 50 ml) and concentrated in an oil pump vacuum. Compound (12) is obtained as a colourless foam (965 mg, 95%). The UV data for compound (12) were identical to the data for (11). 1H-NMR [(D6)-DMSO]: 1.82 (m, J2'β, 2'α=14.5 Hz, H-2'β); 2.57 (m, 1H, H-2'α); 3.68 (m, 2H, H-5'); 3.81 (m, 1H, H-4'); 4.23 (m, 1H, H-3'); 4.73 (br s, 1H, 5'-OH); 5.19

(br s, 1H, 3'-OH); 5.73 (d, J5,6=7.25 Hz, 1H, H-5); 6.02 (m, 1H, H-1'); 7.11 (br s, 2H, NH2); 7.84 (d, 1H, H-6).

EXAMPLE 27

1-(4-benzoylamino-2'-deoxy-β-D-threo-pentofuranosyl]-cytosine (13) [4]

Nucleoside 12 (454 mg, 2 mmol) which has previously been dried three times by evaporation with dry pyridine, is suspended in absolute pyridine (10 ml) and admixed with $(CH_3)_3SiCl$ (1.28 ml, 10 mmol) under argon. The solution is stirred for 15 minutes, afterwards benzoyl chloride (0.87 ml, 10 mmol) is added and the solution is stirred for 2 h at room temperature. Subsequently the mixture is cooled in an ice bath and water (2 ml) is added. After addition of 25% ammonia solution (2 ml) it is stirred for a further 15 minutes at room temperature. The solution is evaporated almost to dryness, the residue is dissolved in water (28 ml) and washed with ethyl acetate (10 ml). After concentrating the aqueous phase by evaporation, product (13) begins to crystallize out on cooling. White needles are obtained by re-crystallization from methanol. (450 mg, 68%) melting point: 177° C. (MeOH). TLC ($CH_2Cl_2/CH_3OH$ 9:1): Rf 0.36. UV (MeOH) λ max (ε)=302, 258 (10500, 22230). $C_{16}H_{17}N_3O_5$ (331.70): calc.: C, 58.01; H, 5.17; N, 12.68. found: C, 58.14; H, 5.29; N, 12.71.

1H-NMR [(d6)-DMSO]: 2.01 (d, JH-2'β, H-2'α=14.5 Hz, 1H, H-2'β,); 2.57 (m, 1H, H-2'α); 3.78 (m, 2H, H-5', H-5"); 3.98 (m, 1H, H-4'); 4.35 (m, 1H, H-3'); 4.76 (t, J5'-OH, H-5', H-5"=5.5 Hz, 1H, 5'-OH); 5.09 (d, J3'-OH, H-3'=2.75, 1H, 3'-OH); 6.00 (dd, J=7.25 Hz, 1H, H-1'); 7.31–8.02 (m, 5H, arom. H); 7.63 (d, JH-5, H-6=7.5 Hz, 1H, H-6); 8.28 (d, JH-6; H-5=7.5 Hz, 1H, H-6); 11.19 (brs, 1H, NH).

EXAMPLE 28

1-[5'-O,4-N-Bis(4,4'-dimethoxytrityl)-2'-deoxy-β-D-threo-pentofuranosyl]cytosine (14a)

Dry (12) (520 mg, 2.2 mmol) which can be obtained by evaporation with dry pyridine, is dissolved in absolute pyridine (10 ml). 4,4'-dimethoxytrityl chloride (1.5 g, 4 mmol) and 4-dimethylaminopyridine (150 mg, 1.26 mmol) is added to this solution.

After five hours the TLC shows almost no more starting material. The reaction mixture is poured into cold saturated sodium hydrogencarbonate solution (50 ml) and extracted with three portions of ethyl acetate (30 ml). The collected organic phases are concentrated by evaporation and the residue is purified by column chromatography (column 6×30 cm, 0.1 bar, $CH_2Cl_2$/MeOH/$Et_3N$ at first 93:5:2, then 88:10:2).

The suitable fractions of the non-polar substance (14a) are collected, the solvent is removed by evaporation, the residue is dissolved in a small amount of dichloromethane and added dropwise while stirring to petroleum ether as a result of which (14a) precipitates as a white solid. (680 mg, 40%).

TLC ($CH_2Cl_2/CH_3OH$ 9:1): Rf 0.46. UV (MeOH): max (ε)=280, 230 (18100, 43000). 1H-NMR [CDCl3]: 2.17 (d, JH-2'β, H-2'α=14.3 Hz, 1H, H-2'β,); 2.52 (m, 1H, H-2'α); 3.46 (m, 2H, H-5', H-5"); 3.74 (s, 12H, OCH3); 3.96 (m, 1H, H-4'); 4.35 (m, 1H, H-3'); 4.99 (d, JH-5, H-6=7.75 Hz, 1H, H-5'); 6.01 (dd, J=6.25 Hz, 1H, H-1'); 6.75–7.38 (m, 26H, arom.H); 7.51 (d, JH-5, H-6=7.75 Hz, 1H, H-6). $C_{51}H_{49}N_3O_8$ (831.96): calc.: C, 73.63; H, 5.94; N, 5.05. found: C, 73.62; H, 6.08; N, 5.06.

EXAMPLE 29

1-[5'-O-(4,4'-dimethoxytrityl)-2'-deoxy-β-D-threo-pentofuranosyl]cytosine (14b) [2]

The fractions of the polar substance (14b) are also collected, the solvent is removed by evaporation, the residue is taken up in a small amount of dichloromethane and added dropwise while stirring to petroleum ether as a result of which (14b) precipitates as a white solid. (580 mg, 55%). TLC ($CH_2Cl_2/CH_3OH$ 9:1) Rf 0.36. UV (MeOH): λ max (ε)=234, 274 (22200, 8970). 1H-NMR [(d6)-DMSO]: 1.80 (d, JH-2'β, H-2'α=14.5 Hz, 1H, H-2'β,); 2.50*) (m, 1H, H-2'α); 3.18 (m, 2H, H-5', H-5"); 3.74 (s, 6H, OCH3); 4.06 (m, 1H, H-4'); 4.15 (m, 1H, H-3'); 5.12 (d, J3'-OH, H-3'=3.70 Hz, 1H, 3'-OH); 5.64 (d, JH-5, H-6=7.43 Hz, 1H, H-1'); 6.04 (dd, J=6.5 Hz, 1H, H-1'); 6.87–7.44 (m, 15H, arom. H); 7.66 (d, JH-5, H-6=7.43 Hz, 1H, H-6). $C_{30}H_{31}N_3O_6$ (529.59): C, 68.04; H, 5.90; N, 7.93. found: C, 68.03; H, 5.93; N, 7.89.

EXAMPLE 30

1-[4-benzoylamino-2'-deoxy-5'-O-(4,4'-dimethoxytrityl)-β-D-threo-pentofuranosyl]cytosine (15)

Method A [8]: compound 13 (270 mg, 0.8 mmol) is dried by evaporation with dry pyridine. The residue is dissolved in absolute pyridine (10 ml). DMT-Cl (0.6 g; 1.8 mmol) and 4-dimethylaminopyridine (200 mg; 1.8 mmol) is added under argon and the solution is stirred for 4 hours at room temperature. The solution is shaken in 5% $NaHCO_3$ solution (27 ml), extracted twice with dichloromethane (50 ml), the collected organic phases are dried over $Na_2SO_4$ and the solvent is removed by evaporation. After repeated evaporation with toluene, the residue is purified by flash chromatography (column 6×20 cm, 0.1 bar, $CH_2Cl_2$/MeOH/$Et_3N$ 93:5:2). The product (15) is precipitated from petroleum ether as a white powder (330 mg, 64%)

Method B: After the processing (without column chromatography), the reaction mixture of (14a) and (14b) is dissolved in absolute pyridine (10 ml). $(CH_3)_3SiCl$ (1.28 ml, 10 mmol) is added to the solution under argon. After 15 minutes benzoyl chloride (1.16 ml, 10 mmol) is added and the reaction mixture is stirred for three hours at room temperature. After cooling to 0° C. water, (2 ml) is added and after a further 5 minutes 25% ammonia solution (4 ml) is added. After stirring for 30 minutes at room temperature, the solution is concentrated by evaporation and the rubber-like residue is extracted in dichloromethane (20 ml) and 5% $NaHCO_3$ solution (40 ml). The aqueous phase is extracted with 2 portions dichloromethane, the organic phases are combined and the solvent is removed by evaporation. The isolation is carried out in the same manner as described above. (530 mg, 36.5%)

TLC ($CH_2Cl_2$/MeOH 9:1): Rf 0.54. UV (MeOH): λ max (ε) 301, 256, 236 (14540, 28880, 37040). 1H-NMR [(d6)-DMSO]: 2.00 (d, JH-2'β, H-2'α=14.5 Hz, 1H, H-2'β); 2.50*) (m, 1H, H-2'α); 3.39 (m, 2H, H-5', H-5"); 3.75 (s, 6H, OCH3); 4.23 (m, 2H, H-4', H-3'); 5.07 (d, J3'-OH, H-3'=2.50 Hz, 1H, 3'-OH); 6.05 (dd,J=7 Hz, 1H, H-1'); 6.89–7.62 (m, 18H, arom.H); 7.53 (d, JH-5, H-6=7.43 Hz, 1H, H-1'); 8.00 (d, JH-5, H-6=7.43 Hz, 1H, H-6); 11.20 (brs, 1H, NH); $C_{37}H_{35}N_3O_7$ (633.70): C, 70.13; H, 5.57; N, 6.63. found: C, 70.15; H, 5.64; N, 6.46.

EXAMPLE 31

1-[4-benzoyl-2'-deoxy-5'-O-(4,4'-dimethoxytrityl)-β-D-threo-pentofuranosyl]cytosine-(3'-hydrogen phosphonate) (16)

$PCl_3$ (500 μl; 5.75 mmol) and 1,2,4-triazole (1.35 g; 19.4 mmol) are added to a solution of N-methylmorpholine (6.5 ml; 57.5 mmol) in 23 ml absolute dichloromethane under argon. The solution is stirred for 30 minutes, after which it is cooled to 0° C. and admixed with (15) (400 mg; 0.63 mmol), which had previously been dried by evaporation with absolute acetonitrile, dissolved in 7 ml absolute dichloromethane and added slowly dropwise at room temperature. After 20 minutes stirring at room temperature, the solution is poured into 32 ml TBK buffer (pH 7.5–8.0) and the phases are separated. The aqueous phase is extracted 4 times with dichloromethane (15 ml), the pooled organic phases are dried over $Na_2SO_4$, filtered and the solvent is removed by evaporation. The light yellow foam is chromatographed (silica gel column 6×20 cm, 0.5 bar, 1 liter $CH_2Cl_2/Et_3N$ 98:2, $CH_2Cl_2/MeOH/Et_3N$ 88:10:2). The residue of the main zone is dissolved in $CH_2Cl_2$ extracted by shaking 10 times with 0.1 M TBK buffer (10 ml), the aqueous phase is reshaken several times with $CH_2Cl_2$, the collected organic phases are dried over $Na_2SO_4$ and the solvent is removed by evaporation. The H-phosphonate is present as a colourless foam (260 mg; 51%).

TLC ($CH_2Cl_2/MeOH/Et_3N$ 88:10:2): Rf 0.35. 1H-NMR [CDCl3]: 1.18 (t, J=7.25 Hz, 9H, 3×CH3CH2NH); 2.47 (d, J H-2'α, H-2'β=−15 Hz, 1H, H-2'β); 2.62 (m, 1H, H-2'α); 2.90 (q, J=7.25 Hz, 6H, 3×CH3CH2NH); 3.55 (m, 2H, 5'-CH2); 3.77 (s, 6H, OCH3); 4.27 (m, 1H, H-4'); 4.78 (m, 1H, H-3'); 5.31, 7.81 (d, JH-P=625 Hz, 1H, H—P); 6.16 ("dd", J=6.75 Hz, 1H, H-1'); 6.80–7.90 (m, 18H, arom H); 7.21 (d, JH-5, H-6=7.25 Hz, 1H, H-5); 8.08 (JH-6,H-5=7.25 Hz, 1H, H-6). 31P-NMR [d6-DMSO]: 0.60 1J(P,H=590 Hz; 3J(P, H—C4'=8.4 Hz). 31P-NMR [CDCl3]: 3.30 1J(P, H=625 Hz; 3J(P, H—C4'=8.9 Hz).

EXAMPLE 32

1-[4-benzoyl-2'-deoxy-5'-O-(4,4'-dimethoxytrityl)-β-D-threo-pentofuranosyl]cytosine-3'-[(2-cyanoethyl)-N,N-diisopropylphosphoramidite [16b]

Compound 16b was prepared and processed as described in [6].

EXAMPLE 33

1-[2'-deoxy-β-D-threo-pentofuranosyl)cysosine 3'-[3-(N-'Fractosil'carbamoyl)propanoate] [16c]

Compound 16c was prepared and processed as described in [6].

Literature References for Examples 15–33

[1] H. Vorbrüggen, K. Krolikiewicz, Liebigs Ann. Chem. 1976, 745.
[2] M. J. Robins, S .G. Wood, N. K. Dalley, P. Herdewijn, J. Balzarini, E. deClercq, J. Med. Chem. 1989, 32, 1763.
[3] S. Czernecki, J. M. Valery, Synthesis 1991, 239
[4] G. S. Ti, B. L. Gaffney, R. A. Jones, J. Amer. Chem. Soc. 1982, 104, 1315.
[5] B. C. Froehler, P. G. Ng, M. D. Mateucci Nucleic Acids Res. 1986, 14, 5399.
[6] H. Rosemeyer, F. Seela, Helv. Chim. Acta 1991, 74, 748.

EXAMPLE 34

Inhibition of HIV Virus Expression by Oligonucleotides According to the Present Invention 5'-xTxTT CCC AGG CTC AGA TCT GGT CxTxT T*-3' (tar region)
5'-xTxTT CGT CGC TGT CTC CGC TTC TTC CTG CCA xTxTT*-3' (rev region)
5'-xTxTC TGC TAG AGA TTT TCC ACA CxTxT T*-3' (primer binding site)
* due to the commercial availability of the CPG carrier material, it was started with unmodified 2'-deoxy-ribothymidine.
Virus HIV III B H 9
Stock Solutions of Oligomers:
  1 mg×ml$^{-1}$ in PBS buffer
Dilution Series of the Oligomers:
  0.05–50 µg×ml$^{-1}$
Test System I:
  MT-2 (T-lymphoblastoid cells)
Test System II:
  PBMC (peripheral blood monocytic cells)
Test procedure:
  $2×10^4$ or $2×10^5$ infected MT-2 or PBMC cells respectively were added to 100 µl in each case of the respective oligonucleotide solution.

After a 7 day incubation at 37° C., it was monitored for syncytia formation and the reduction of the cytoplastic effect was measured by means of a colour test with MTT or a p24 ELISA. The results are shown in Table I.

TABLE I

| Oligonucleotide region | Concentration µg/ml | CPE reduction % |
| --- | --- | --- |
| tar | 0.05 | 59.1 |
| rev | 0.05 | 40.7 |
| pbs | 0.05 | 42.2 |

Any oligonucleotides according to the present invention (e.g. analogous to example 11 and 22) can be synthesized using the monomers described in the examples.

EXAMPLE 35

1-(2-deoxy-β-D-threo-pentofuranosyl)thymine cyclic 3',5'-monophosphates, triethylammonium (2)

General information concerning the production of deoxyxylonucleoside-5'-mono, di and triphosphates In order to produce the 5' mono, di or triphosphates, the 3'-OH group is firstly benzoylated and then it is phosphorylated with $POCl_3$ in trialkylphosphate, preferably trimethylphosphate or triethylphosphate to form 5'-phosphate. Subsequently the 3' protecting group is removed with a base such as ammonia, during which a corresponding protecting group which has been introduced into the heterocyclic base in some nucleotides is also cleaved off if necessary. A corresponding protecting group strategy can also be applied to the production of thiophosphates.

A solution of (1-(2-deoxy-β-D-threo-pentofuranosyl)-thymine (1) (59 mg, 0.24 mmol) in trimethylphosphate (1 ml) is incubated for five hours at 4° C. with $POCl_3$ (40 µl, 0.42 mmol).

Triethylammonium bicarbonate (1 mol, pH 7.6, 10 ml) is added and the reaction mixture is concentrated by evaporation after stirring for one hour at room temperature.

The residue is chromatographed on DEAE Sephadex ($HCO_3^-$ form, column 30×2 cm). The chromatography is carried out with 400 ml water and subsequently with a linear gradient of triethylammonium bicarbonate (0–0.3 mol/l, 1200 ml). The cyclophosphate elutes at 0.2 mol/l. The fractions containing the product are concentrated by evaporation, taken up three times in 50 ml water and again concentrated by evaporation.

The product is again chromatographed on DEAE Sephadex under the same conditions. The vapourizable salts are removed by repeated co-evaporation with water, ethanol and acetone.

1394 $A_{267}$ units (65%) of a colourless solid. TLC (2-propanol/25% aq. ammonia/water, 7:1:1): $R_f$ 0.45; (EtOAc/acetone/EtOH/water, 15:3:4:3): $R_f$ 0.09. HPLC (5% MeCN in 0.1 M triethylammonium acetate, pH 7.0; 0.6 ml/min): $t_R$ 14.9 min.

Electrophoresis: $E_{UP}$ 0.64. UV (MeOH): $\lambda_{max}$ 267 nm. $^{31}$P-NMR ($D_2O$/0.1 M Tris-HCl buffer, 1:1) −5.03 (d, J=17.3). $^1$H-NMR (($D_6$)DMSO): 11.28 (s, NH); 10.79 (br, NH); 7.87 (s, H—C(6)); 6.12 (d, J=7.9, H—C(1')); 4.69 (br, H—C(3')); 4.40–4.14 (m, $CH_2$(5')); 3.64 (br, H—C(4')); 3.04 (q, $CH_2$(Et)); 2.66 (m, $H_\alpha$—C(2')); 1.96 (d, J=−16.2, $H_\beta$—C(2')); 1.76 (s, Me—C(5)); 1.20 (t, Me—(Et)).

EXAMPLE 36

9-(2-deoxy-β-D-threo-pentofuranosyl)adenine cyclic 3',5'-monophosphates, triethylammonium (4a)

Method A:

The reaction of compound 3 (9-(2-deoxy-β-D-threo-pentofuranosyl)adenine (25 mg, 0.1 mmol) with $POCl_3$ is carried out in trimethyl phosphate as described for compound 2 in example 35 but in the presence of 2-t-butylimino-2-diethyl-amino-1,3-dimethyl-perhydrodiazaphosphorine (BEMP) (41 mg, 0.15 mmol). The reaction is completed after 12 hours. The processing is carried out as described in example 35. The final purification after chromatography on Sephadex is carried out by thin layer chromatography using EtOAc/acetone/EtOH/water, 15:3:4:3 as the solvent system ($R_f$ 0.13).

Method B:

The reaction is carried out with compound 3 (20 mg, 0.08 mmol) as described for method A but without addition of BEMP. After chromatography on DEAE Sephadex adenine (5 mg, 46%) is firstly eluted with water and then compound 4a) is eluted with butter. A colourless substance is obtained (567 $A_{260}$ untis, 39%).

Method C:

$POCl_3$ (20 μl, 0.21 mmol) is added to a solution of imidazole (86 mg, 1.26 mmol) in MeCN (0.5 ml). It is stirred for 30 minutes at room temperature, cooled to 0° C. and the solution of 9b) (35 mg, 0.1 mmol) in MeCN/dimethylformamide (1:1, 1 ml) is added. The reaction mixture is incubated for 2 hours at 4° C. and subsequently for 14 hours at room temperature. After neutralization with 1 mol/l aqueous triethylammonium bicarbonate (12 ml), the solution is stirred for 1 hour and concentrated by evaporation. The residue is treated with 25% aqueous ammonia solution (20 ml) for 16 hours and concentrated by evaporation. The purification of compound 4a) is carried out on DEAE Sephadex as described. The unprotected nucleoside 3 is obtained after elution with water (24%), compound 4a) is obtained as a colourless compound (843 $A_{260}$ units, 57%) using a solution of 0.2 mol/l triethylammonium bicarbonate.

EXAMPLE 37

1-[3-O-benzyol-2-deoxy-5-O-(4,4'-dimethoxytriphenyl-methyl)-β-D-threo-pentofuranosyl]thymine (6a)

Benzoyl cyanide (75 mg, 0.57 mmol) and triethylamine (80 μl, 0.57 mmol) are added to a solution of compound 5a) (265 mg, 0.49 mmol) in MeCN (4 ml). It is stirred for 1 hour at room temperature, concentrated by evaporation and the residue is chromatographed on a silica gel column (2×17 cm) in $CH_2Cl_2$/acetone, 6:1. Compound 6a) is obtained as a white foam (255 mg, 81%).

TLC ($CH_2Cl_2$/acetone, 6:1): $R_f$ 0.56. $^1$H-NMR (($D_6$) DMSO): 11.32 (s, NH); 7.72–7.17 (m, 14 arom. H and H—C(6)); 6.80–6.61 (m, 4 arom. H); 6.18 (d, J=5.7, H—C (1')); 5.68 (m, H—C(3')); 4.48 (m, H—C(4')); 3.69 (m, $CH_2$(5') and 2s, 2 MeO); 2.88 (m, $H_\alpha$—C(2')); 2.26 (d, J=−16.2, $H_\beta$—C (2') 1.55 (s, Me). Anal. calcd. for $C_{38}H_{36}N_2O_8$ (648.71): C, 70.36; H, 5.59; N, 4.32. found: C, 70.31; H, 5.70; N, 4.36.

EXAMPLE 38

1-(3-O-benzoyl-2-deoxy-β-D-threo-pentofuranosyl) thymine (7a)

The solution of 6a) (200 mg, 0.31 mmol) in 80% acetic acid (3 ml) is stirred for 15 minutes at room temperature, diluted with 100 ml and concentrated by evaporation. The residue is taken up once each time with 50 ml water, 2-propanol (50 ml) and 50 ml methanol, concentrated by evaporation and chromatographed on silica gel (2×12 cm) in $CH_2Cl_2$/MeOH 95:5 in which compound 7a) is obtained as a white foam (98 mg, 92%).

TLC ($CH_2Cl_2$/MeOH, 95:5): $R_f$ 0.30. $^1$H-NMR (($D_6$) DMSO): 11.29 (s, NH); 7.98–7.51 (m, 5 arom. H and H—C(6)); 6.14 (dd, J=7.8, 2.3, H—C(1')); 5.54 (m, H—C (3')); 4.98 (t, OH—C(3')); 4.19 (m, H—C(4')); 3.82 (m, $CH_2$ (5')); 2.87 (m, $H_\alpha$—C(2')); 2.20 (dd, J=−15.4, 2.0 $H_\beta$—C (2')); 1.69 (s, Me). Anal. calcd. for $C_{17}H_{18}N_2O_6$ (346.34): C, 58.96; H, 5.24; N, 8.09. found: C, 59.11; H, 5.35; N, 7.99.

EXAMPLE 39

1-(2-deoxy-β-D-threo-pentofuranosyl)thymine 5'-monophosphate, triethylammonium (8a)

Method A:

The solution of compound 7a) (80 mg, 0.23 mmol) in PO $(OMe)_3$ (0.5 ml) is incubated for 8 hours at 4° C. with $POCl_3$ (46 μl, 0.48 mmol). The reaction mixture is added to cold 1 molar aqueous triethylammonium bicarbonate (15 ml), incubated for two hours at room temperature, concentrated by evaporation and again taken up twice in water (50 ml) and concentrated by evaporation. The residue is incubated for three hours with 25% aqueous ammonia colution (50 ml), concentrated by evaporation and chromatographed on DEAE Sephadex ($HCO_3^-$ form, 2×30 cm). It is eluted with water (600 ml) and then with a linear gradient of triethylammonium bicarbonate (0–0.3 mol/l, 1200 ml). The fractions that contain phosphate elute at 0.2–0.25 mol/l. They are concentrated by evaporation, again taken up in water and concentrated and again chromatographed on DEAE Sephadex under the same conditions. Triethylammonium bicarbonate is removed by repeated evaporation with water and ethanol. A colourless amorphous product is obtained.

(1443 $A_{267}$ units, 71%). TLC (EtOAc/acetone/EtOH/water, 15:3:4:3): $R_f$ 0.06, (2-propanol/25% aq. ammonia/water, 7:1:1): $R_f$ 0.10. HPLC (0.1 M triethylammonium acetate/5% MeCN; 0.6 ml/min): $t_R$ 8 min. Electrophoresis: $E_{UP}$ 0.87. UV ($H_2O$): $\lambda_{max}$ 267 nm. $^{31}$P-NMR ($D_2O$/0.1 M Tris-HCl buffer): 1.36

Method B:

9-[2-deoxy-5-O-(4,4'-dimethoxytriphenylmethyl)-β-D-threo-pentofuranosyl]adenine (5b)

The compound is obtained from compound 7a) (80 mg, 0.23 mmol) as in method A. Only the removal of the benzoyl group is carried out with 0.1 mol/l NaOH in 50% aqueous methanol (15 ml) at 50° C. for two hours. The solution is neutralized with Dowex 50 (H⁺ form), the ion exchanger is removed by filtration and the neutral solution is concentrated by evaporation. The further purification is carried out as described in method A. 1214 $A_{276}$ units (60%) are obtained.

EXAMPLE 40

Compound 3 (300 mg, 1.19 mmol) in pyridine (15 ml) is incubated with 4,4'-dimethoxytrityl chloride (508 mg, 1.5 mmol) and ethyldiisopropylamine (255 µl, 1.5 mmol) for 12 hours at room temperature. The solution is concentrated by evaporation at 30° C. The residue is again taken up in toluene, concentrated by evaporation and chromatographed on silica gel (4×11 cm).

$CH_2CL_2$/acetone/$Et_3N$ (40:40:3), White foam (476 mg, 72%). TLC ($CH_2Cl_2$/acetone/$Et_3N$, 40:40:3): $R_f$ 0.64. ¹H-NMR (($D_6$)DMSO): 8.26 (s, H—C6)); 8.16 (s, H—C (2)); 7.41–7.18 (m, 9 arom. H, $NH_2$); 6.84–6.77 (m, 4 arom. H); 6.35 (d, J=8.2, H—C(1')); 5.94 (d, J=5.2, OH—C(3')); 4.32 (m, H—C(3')); 4.19 (m, H—C(4')); 3.71 (s, 2 OMe) 3.23–3.02 (m, $CH_2$-(5'); 2.78 (m, $H_\alpha$—C(2')); 2.29 (d, J=-14.8, $H_\beta$C(2')).

EXAMPLE 41

9-[3-O-benzoyl-2-deoxy-5-O-(4,4'-dimethoxytriphenyl-methyl)-β-D-threo-pentofuranosyl]adenine (6b)

The solution of compound 5b) (400 mg, 0.72 mmol) in MeCN (4 ml) is incubated with benzoyl cyanide (105 mg, 0.8 mmol) and triethylamine (130 µl, 0.39 mmol) at room temperature for three hours. 25 mg (0.19 mmol) benzyl cyanide and 25 µl triethylamine are in addition added and it is stirred for a further 15 hours. The solution is concentrated by evaporation and the residue is chromatographed on silica gel (2×15 cm) using $CH_2Cl_2$/acetone (1:2) to give a white foam (305 mg, 64%). TLC ($CH_2Cl_2$/acetone, 1:2): $R_f$ 0.60. ¹H-NMR (($D_6$)DMSO): 8.09 (s, H—C(8)); 8.07 (s, H—C (2)); 7.68–7.13 (m, 14 arom. H, $NH_2$); 6.75–6.69 (m, 4 arom. H); 6.41 (d, J=5.2, H—C(1')); 5.82 (m, H—C(3')); 4.57 (m, H—C(4')); 3.69 (s, OMe); 3.67 (s, OMe); ca 3.3–3.2 (m, $CH_2$(5')); 3.05 (m, $H_\alpha$—C(2')); 2.91 (d, J=-14.3, $H_\beta$—C (2')).

EXAMPLE 42

9-(3-O-benzoyl-2-deoxy-β-D-threo-pentofuranosyl) adenine (7b)

Compound 6b) (260 mg, 0.40 mmol) is taken up in 80% acetic acid (10 ml) and stirred for 80 minutes at room temperature. The solution is diluted with 50 ml water and concentrated by evaporation. The residue is taken up twice with 20 ml water each time and once in 20 ml 2-propanol and concentrated by evaporation. The product is purified on silica gel (2×12 cm) and chromatographed in $CH_2Cl_2$/MeOH 93:7, Colourless solid (120 mg, 85%). M.p. 166–168° C. (2-propanol).

TLC ($CH_2Cl_2$/MeOH, 93:7): $R_f$ 0.30. ¹H-NMR (($D_6$) DMSO): 8.28 (s, H—C(8)); 8.07 (s, H—C(2)); 7.85–7.47 (m, 5 arom. H); 7.27 (s, $NH_2$); 6.38 (d, J=5.2, H—C(1')); 5.68 (m, H—C(3')); 5.01 (br, OH—C(5')); 4.33 (m, H—C (4')); 3.76 (m, H—C(5')); 3.02 (m, $H_\alpha$—C(2')); 2.83 (d, J=-14.7, $H_\beta$—C(2')); Anal. calcd. for $C_{17}H_{17}N_5O_4$ (355.35): C, 57.46; H, 4.82; N, 19.71. found: C, 57.15; H, 5.02; N, 19.49.

EXAMPLE 43

9-(2-deoxy-β-D-threo-pentofuranosyl)adenine 5'-phosphate, triethylammonium (8b).

Compound 8b) is prepared from compound 7b) (53 mg, 0.15 mmol) as in method A for the production of compound 8a). The duration of the $POCl_3$ treatment is 4 hours. An amorphous product (1222 $A_{258}$ units, 53%) is obtained. The product is dissolved in ca. 200 gl methanol and precipitated with 20 ml ether. The precipitate is separated by centrifugation and dried over phosphorus pentoxide. Thin layer chromatography is carried out with 2-propanol/25% ammonia/water, 7:1:2): $R_f$ 0.24, (EtOA/acetone/EtOH/water, 15:3:4:3): $R_f$ 0.06. HPLC (0.1 M triethylammonium acetate/5% MeCN; 0.6 ml/min) $t_R$ 13 min. Electrophoresis: $E_{UP}$ 0.68. UV (MeOH): $\lambda_{max}$259 nm. ³¹P-NMR ($D_2O$/MeOD, 1:1): 2.94. ¹H-NMR ($D_2O$/MeOD, 1:1): 9.89 (s, H—C(8)); 9.71 (s, H—C(2)); 7.84 (d, J=8.0, H—C(1')); 6.08 (m, H—C(3')); 5.77–5.61 (m, $CH_2$(5')); 5.01 (m, H—C (4')); 4.68 (q, $CH_2$); 4.48 (m, $H_\alpha$—C(2')); 3.92 (d, $H_\beta$—C (2')); 2.74 (m, $CH_3$).

EXAMPLE 44

Compound 5a) is prepared analogous to

Rosemeyer, H.; Seela, F. Helv. Chim. Acta 1991, 74, 748.
Rosemeyer, H.; Krecmerova M.; Seela F. Helv. Chim. Acta, 1991, 74, 2054.
Fox, J. J.; Miller, N. C. J. Org. Chem. 1963, 28, 936.

Data for compound 4a):

824 $A_{260}$ units (53.8%) of colourless solid TLC (2-propanol/25% aqueous ammonia/water, 7:1:1): $R_f$ 0.54. HPLC (5% MeCN in 0.1 M triethylammonium acetate, pH 7, 0.6 ml/min): $t_R$ 15 min. Electrophoresis: $E_{UP}$ 0.35. UV (MeOH): $\lambda_{max}$260 nm. ³¹P-NMR ($D_2O$/0.1 M Tris-HCl buffer, 1:1): -5.11 (d, J=19.4). ¹H-NMR (($D_6$)DMSO): 9.97 (br, NH); 8.33 (s, H—C(8)); 8.15 (s, H—C(2)); 7.34 (s, $NH_2$); 6.40 (d, J=7.8, H—C(1')); 4.63 (br, H—C(3')); 4.42–4.10 (m, $CH_2$(5')); 3.94 (br, H—C(4')); 3.05 (q, $CH_2$); 2.85 (m, $H_\alpha$—C(2')); 2.28 (d, J=-14.6, $H_\beta$—C(2')); 1.18 (t, Me).

What is claimed is:

1. An oligodeoxyribonucleotide in which at least two of the 2'-deoxy-β-D-erythro-pentofuranosyl groups have been replaced by 2'-deoxy-β-D-threo-pentofuranosyl groups, wherein at least the 2'-deoxy-β-D-erythro-pentofuranosyl groups at both the 5' end and the 3' end have been replaced by a 2'-deoxy-β-D-threo-pentofuranosyl group and wherein said oligodeoxyribonucleotide consists of 6 to 100 nucleotides, the oligonucleotide further comprising a deoxyxylonucleotide comprising a base of at least one of A, T, C, G or a modified base.

2. An oligodeoxyribonucleotide in which at least 20% of the 2'-deoxy-β-D-erythro-pentofuranosyl groups in consecutive nucleotides are replaced by 2'-deoxy-β-D-threo-pentofuranosyl groups, wherein said oligodeoxyribonucleotide consists of 6 to 100 nucleotides.

3. The oligodeoxyribonucleotide according to claim 1, wherein said oligodeoxyribonucleotide consists of 15 to 30 nucleotide building blocks.

4. An oligodeoxyribonucleotide according to claim 2, wherein said oligodeoxyribonucleotide consists of 15 to 30 nucleotide building blocks.

5. An oligodeoxyribonucleotide according to claim 1, wherein at least 30% of the 2'-deoxy-β-D-erythro-pentofuranosyl groups are replaced by 2'-deoxy-β-D-threo-pentofuranosyl groups.

6. The oligodeoxyribonucleotide according to claim 2, wherein at least 30% of the 2'-deoxy-β-D-erythro-pentofuranosyl groups are replaced by 2'-deoxy-β-D-threo-pentofuranosyl groups.

7. The oligodeoxyribonucleotide according to claim 1, wherein all 2'-deoxy-β-D-erythro-pentofuranosyl groups are replaced by 2'-deoxy-β-D-threo-pentofuranosyl groups.

8. The oligodeoxyribonucleotide according to claim 2, wherein all 2'-deoxy-β-D-erythro-pentofuranosyl groups are replaced by 2'-deoxy-β-D-threo-pentofuranosyl groups.

9. The oligodeoxyribonucleotide according to claim 1, wherein at least one nucleotide building block is replaced by a 2'-deoxylonucleotide at a recognition sequence for endonucleases in the oligonucleotide.

10. The oligodeoxyribonucleotide according to claim 2, wherein at least one nucleotide building block is replaced by a 2'-deoxylonucleotide at a recognition sequence for endonucleases in the oligonucleotide.

11. The oligodeoxyribonucleotide according to claim 1, wherein said oligodeoxyribonucleotide contains at least one modified base.

12. The oligodeoxyribonucleotide according to claim 2, wherein said oligodeoxyribonucleotide contains at least one modified base.

13. The oligodeoxyribonucleotide according to claim 11, wherein the modified base is selected from the group consisting of 1-deazadenine, 3-deazadenine, 7-deazadenine, 1-deazaguanine, 3-deazaguanine, 7-deazaguanine, 1-deazahypoxanthine, 3-deazahypoxanthine, 7-deazahypoxanthine, 7-deazapurines substituted at C-7, purines substituted at C-8, and pyrimidines substituted at C-5.

14. The oligodeoxyribonucleotide as claimed in claim 12, wherein the modified base is selected from the group consisting of 1-deazadenine, 3-deazadenine, 7-deazadenine, 1-deazaguanine, 3-deazaguanine, 7-deazaguanine, 1-deazahypoxanthine, 3-deaza-hypoxanthine, 7-deazahypoxanthine, 7-deazapurines substituted at C-7, purines substituted at C-8, and pyrimidines substituted at C-5.

15. The oligodeoxyribonucleotide according to claim 1, further comprising hydrogen, a reporter group or an intercalator group at the 5' end, the 3' end or both the 5' end and the 3' end.

16. The oligodeoxyribonucleotide according to claim 2, further comprising hydrogen, a reporter group or an intercalator group at the 5' end, the 3' end or both the 5' end and the 3' end.

17. The oligonucleotides according to claim 15, comprising a monophosphate group at the 5' end.

18. The oligonucleotide as claimed in claim 16, comprising a monophosphate group at the 5' end.

19. A process for the production of an oligodeoxyribonucleotide according to claim 1 comprising a process of oligonucleotide synthesis in which a) a start nucleoside is bound to a solid support;

b) the desired oligonucleotide is synthesized by stepwise coupling with appropriately activated monomeric nucleotide building blocks, wherein the nucleotide building blocks comprise protective groups on the heterocyclic bases and on the 5' OH, the 3' OH or both the 5' OH and the 3' OH;

c) the oligonucleotide is cleaved from the support using a base;

d) heterocyclic protecting groups are cleaved with a base; and e) the 5' protecting group is cleaved with an acid.

20. The process according to claim 19, further comprising purifying the oligonucleotide.

21. The process according to claim 19, wherein trivalent phosphorus is oxidized to pentavalent phosphorus during and after the synthesis.

22. A process for the production of oligodeoxyribonucleotide according to claim 2, in which a) a start nucleotide is bound to a solid support;

b) the desired oligonucleotide is synthesized by stepwise coupling with appropriately activated monomeric nucleotide building blocks, wherein the nucleotide building blocks comprise protective groups on the heterocyclic bases and on the 5' OH, the 3' OH or both the 5' OH and the 3' OH, c) the oligonucleotide is cleaved from the support using a base;

d) heterocyclic protecting groups are cleaved with a base; and e) the 5' protecting group is cleaved with an acid.

23. The process according to claim 22, further comprising purifying the oligonucleotide.

24. The process according to claim 22, wherein trivalent phosphorus is oxidized to pentavalent phosphorus during and after the synthesis.

25. A pharmaceutical composition suitable for the treatment of viral infections comprising an oligodeoxyribonucleotide in which at least two of the 2'-deoxy-β-D-erythro-pentofuranosyl groups have been replaced by 2'-deoxy-β-D-threo-pentofuranosyl groups, wherein at least the 2'-deoxy-β-D-erythro-pentofuranosyl groups at both the 5' end and the 3' end have been replaced by a 2'-deoxy-β-D-threo-pentofuranosyl group and wherein said oligodeoxyribonucleotide consists of 6 to 100 nucleotides; and a pharmaceutically acceptable carrier.

26. A pharmaceutical composition suitable for the treatment of viral infections comprising an oligodeoxyribonucleotide in which at least 20% of the 2'-deoxy-β-D-erythro-pentofuranosyl groups in consecutive nucleotides are replaced by 2'-deoxy-β-D-threo-pentofuranosyl groups, wherein said oligodeoxyribonucleotide consists of 6 to 100 nucleotides; and a pharmaceutically acceptable carrier.

27. A composition comprising a) oligodeoxyribonucleotides in which at least 30% of the 2'-deoxy-β-D-erythro-pentofuranosyl groups in consecutive nucleotides have been replaced by 2β-deoxy-β-D-threo-pentofuranosyl groups, wherein said oligodeoxyribonucleotides consist of 6 to 100 nucleotides; and b) a pharmaceutically acceptable carrier.

* * * * *